(12) United States Patent
Hess et al.

(10) Patent No.: US 9,078,695 B2
(45) Date of Patent: Jul. 14, 2015

(54) METHODS AND DEVICES FOR ACCESSING A BODY CAVITY USING A SURGICAL ACCESS DEVICE WITH MODULAR SEAL COMPONENTS

(75) Inventors: Christopher J. Hess, Cincinnati, OH (US); Kyle P. Moore, Mason, OH (US); Daniel H. Duke, West Chester, OH (US); Daniel J. Mumaw, Cincinnati, OH (US); Katherine J. Schmid, Cincinnati, OH (US); Michael S. Cropper, Edgewood, KY (US); Jeffrey David Messerly, Cincinnati, OH (US); William Bruce Weisenburgh, II, Maineville, OH (US); Jerome R. Morgan, Cincinnati, OH (US); Michael D. Cronin, Cincinnati, OH (US); Denzel Z. Herrera-Davis, Cincinnati, OH (US); Gregory W. Johnson, Milford, OH (US); Kevin L. Houser, Springdale, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 943 days.

(21) Appl. No.: 12/479,395

(22) Filed: Jun. 5, 2009

(65) Prior Publication Data
US 2010/0312063 A1   Dec. 9, 2010

(51) Int. Cl.
*A61B 17/32*   (2006.01)
*A61B 17/34*   (2006.01)
*A61B 17/00*   (2006.01)

(52) U.S. Cl.
CPC ......... *A61B 17/3423* (2013.01); *A61B 17/3462* (2013.01); *A61B 2017/00287* (2013.01);
(Continued)

(58) Field of Classification Search
CPC ............... A61B 17/02; A61B 17/0218; A61B 17/0469; A61B 17/34; A61B 17/3415; A61B 17/3417; A61B 17/3421; A61B 17/3423; A61B 17/3431; A61B 17/3439; A61B 17/3462
USPC .................................................. 600/201–229
See application file for complete search history.

(56) References Cited

U.S. PATENT DOCUMENTS 2,129,391 A   9/1938   Wappler
3,402,710 A   9/1968   Paleschuck
(Continued)

FOREIGN PATENT DOCUMENTS

DE   19814576 A1   10/1999
DE   20022005 U1   4/2001
(Continued)

OTHER PUBLICATIONS

International Search Report and Written Opinion for International App. No. PCT/US2010/036811 dated Sep. 14, 2010 (6 pages).
(Continued)

*Primary Examiner* — Eduardo C Robert
*Assistant Examiner* — Michelle C Eckman
(74) *Attorney, Agent, or Firm* — Mintz Levin Cohn Ferris Glovsky and Popeo, P.C.

(57) ABSTRACT

Methods and devices are provided for providing access through tissue to a surgical site. In one embodiment, a surgical access device can include a hollow tubular member and a modular seal member. The modular seal member can be configured to radially span a lumen of the tubular member and can be removably and replaceably matable to a portion of the tubular member. The access device can also include a plurality of access ports, each of which can be configured to mate with the modular seal member at a respective desired location.

19 Claims, 22 Drawing Sheets

(52) U.S. Cl.
CPC . *A61B2017/3445* (2013.01); *A61B 2017/3449* (2013.01); *A61B 2017/3466* (2013.01); *A61B 2017/3484* (2013.01); *A61B 2017/3488* (2013.01)

(56) References Cited

U.S. PATENT DOCUMENTS

| | | |
|---|---|---|
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,524,644 A * | 6/1996 | Crook .......................... 128/888 |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Pasqualucci et al. |
| 6,706,033 B1 | 3/2004 | Martinez et al. |
| 6,706,050 B1 | 3/2004 | Giannadakis |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,163,525 B2 | 1/2007 | Franer |
| 7,214,185 B1 | 5/2007 | Rosney et al. |
| 7,229,408 B2 | 6/2007 | Douglas et al. |
| 7,297,106 B2 * | 11/2007 | Yamada et al. ............... 600/208 |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 7,998,068 B2 * | 8/2011 | Bonadio et al. ............... 600/208 |
| 8,033,995 B2 * | 10/2011 | Cropper et al. ............... 600/207 |
| 2002/0156432 A1 | 10/2002 | Racenet et al. |
| 2003/0014076 A1 * | 1/2003 | Mollenauer et al. .......... 606/213 |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0015561 A1 | 1/2005 | Matsuda |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 * | 7/2005 | Vaugh et al. .................. 600/206 |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |

(56) References Cited

U.S. PATENT DOCUMENTS

| | | |
|---|---|---|
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0161050 A1* | 7/2006 | Butler et al. .................. 600/208 |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1* | 11/2006 | Bonadio et al. .............. 600/208 |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088204 A1 | 4/2007 | Albrecht et al. |
| 2007/0088258 A1 | 4/2007 | Wenchell et al. |
| 2007/0088277 A1 | 4/2007 | McGinley et al. |
| 2007/0118021 A1 | 5/2007 | Pokorney |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0208312 A1 | 9/2007 | Norton et al. |
| 2007/0255219 A1 | 11/2007 | Vaugh et al. |
| 2008/0009797 A1 | 1/2008 | Stellon et al. |
| 2008/0025519 A1 | 1/2008 | Yu et al. |
| 2008/0027476 A1 | 1/2008 | Piskun |
| 2008/0051739 A1 | 2/2008 | McFarlane |
| 2008/0058728 A1 | 3/2008 | Soltz et al. |
| 2008/0065021 A1 | 3/2008 | Jenkins et al. |
| 2008/0086080 A1 | 4/2008 | Mastri et al. |
| 2008/0119821 A1 | 5/2008 | Agnihotri et al. |
| 2008/0132765 A1 | 6/2008 | Beckman et al. |
| 2008/0255519 A1 | 10/2008 | Piskun et al. |
| 2008/0281161 A1* | 11/2008 | Albrecht et al. .............. 600/206 |
| 2009/0005799 A1 | 1/2009 | Franer et al. |
| 2009/0082731 A1 | 3/2009 | Moreno |
| 2009/0118587 A1 | 5/2009 | Voegele et al. |
| 2009/0187079 A1 | 7/2009 | Albrecht et al. |
| 2009/0227843 A1* | 9/2009 | Smith et al. .................. 600/208 |
| 2009/0270685 A1 | 10/2009 | Moreno et al. |
| 2009/0270686 A1 | 10/2009 | Duke et al. |
| 2009/0270818 A1 | 10/2009 | Duke |
| 2010/0010310 A1 | 1/2010 | Weisenburgh, II et al. |
| 2010/0081863 A1 | 4/2010 | Hess et al. |
| 2010/0081864 A1 | 4/2010 | Hess et al. |
| 2010/0081871 A1 | 4/2010 | Widenhouse et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0240960 A1* | 9/2010 | Richard ........................ 600/208 |
| 2010/0249525 A1 | 9/2010 | Shelton, IV et al. |
| 2010/0261970 A1 | 10/2010 | Shelton, IV et al. |
| 2010/0261972 A1* | 10/2010 | Widenhouse et al. ........ 600/206 |
| 2010/0261974 A1 | 10/2010 | Shelton, IV et al. |
| 2010/0262080 A1 | 10/2010 | Shelton, IV et al. |
| 2010/0268162 A1 | 10/2010 | Shelton, IV et al. |
| 2010/0274093 A1 | 10/2010 | Shelton, IV |
| 2010/0280327 A1 | 11/2010 | Nobis et al. |
| 2010/0286484 A1* | 11/2010 | Stellon et al. ................. 600/208 |
| 2010/0312060 A1 | 12/2010 | Widenhouse et al. |
| 2010/0312061 A1* | 12/2010 | Hess et al. .................... 600/201 |
| 2010/0312062 A1 | 12/2010 | Cropper et al. |
| 2010/0312063 A1* | 12/2010 | Hess et al. .................... 600/204 |
| 2010/0312064 A1 | 12/2010 | Weisenburgh, II et al. |
| 2010/0312065 A1 | 12/2010 | Shelton, IV et al. |
| 2010/0312066 A1* | 12/2010 | Cropper et al. ............... 600/207 |
| 2010/0312189 A1 | 12/2010 | Shelton, IV et al. |
| 2011/0046449 A1* | 2/2011 | Minnelli et al. .............. 600/205 |
| 2011/0124970 A1* | 5/2011 | Kleyman ...................... 600/208 |
| 2011/0295074 A1* | 12/2011 | Stefanchik et al. ........... 600/201 |
| 2011/0295077 A1* | 12/2011 | Stefanchik et al. ........... 600/210 |
| 2012/0029297 A1* | 2/2012 | Bonadio et al. ............... 600/208 |
| 2012/0136214 A1* | 5/2012 | Wenchell ...................... 600/208 |
| 2012/0157777 A1* | 6/2012 | Okoniewski .................. 600/201 |

FOREIGN PATENT DOCUMENTS

| | | |
|---|---|---|
| EP | 0568383 | 11/1993 |
| EP | 568383 A1 | 11/1993 |
| EP | 577400 A1 | 1/1994 |
| EP | 0637431 A1 | 2/1995 |
| EP | 0646358 | 4/1995 |
| EP | 646358 A1 | 4/1995 |
| EP | 709918 | 5/1996 |
| EP | 0776231 A1 | 6/1997 |
| EP | 0776231 B1 | 6/1997 |
| EP | 950376 | 10/1999 |
| EP | 1219251 A1 | 7/2002 |
| EP | 1219251 A1 | 7/2002 |
| EP | 1219252 A1 | 7/2002 |
| EP | 1219252 A1 | 7/2002 |
| EP | 1219253 A1 | 7/2002 |
| EP | 1219253 A1 | 7/2002 |
| EP | 1350476 | 10/2003 |
| EP | 1702575 A2 | 9/2006 |
| EP | 1731105 A1 | 12/2006 |
| EP | 1731105 A1 | 12/2006 |
| EP | 1774918 A1 | 4/2007 |
| EP | 2119404 A1 | 11/2009 |
| EP | 2119404 A1 | 11/2009 |
| FR | 2710270 | 3/1995 |
| FR | 2710270 A1 | 3/1995 |
| JP | 2006320750 | 11/2006 |
| WO | 9407552 A1 | 4/1994 |
| WO | 9602297 A1 | 2/1996 |
| WO | 9608897 A1 | 3/1996 |
| WO | 9636283 A1 | 11/1996 |
| WO | 9743958 A1 | 11/1997 |
| WO | 0032263 A1 | 6/2000 |
| WO | 0041759 A1 | 7/2000 |
| WO | 0108563 A2 | 2/2001 |
| WO | 0217800 A2 | 3/2002 |
| WO | WO-0217800 A2 | 3/2002 |
| WO | 2004030515 A2 | 4/2004 |
| WO | 200500454 A1 | 1/2005 |
| WO | 2005002454 A1 | 1/2005 |
| WO | 2005087112 A1 | 9/2005 |
| WO | WO-2005087112 A1 | 9/2005 |
| WO | 2005094432 A2 | 10/2005 |
| WO | 2005097019 A2 | 10/2005 |
| WO | 2005097234 A2 | 10/2005 |
| WO | WO-2005094432 A2 | 10/2005 |
| WO | 2006057982 A2 | 6/2006 |
| WO | 2007008741 A1 | 1/2007 |
| WO | 2007119232 A2 | 10/2007 |

(56) References Cited

FOREIGN PATENT DOCUMENTS

| WO | WO-2007119232 | A2 | 10/2007 |
|---|---|---|---|
| WO | 2008024502 | A2 | 2/2008 |
| WO | WO-2008024502 | | 2/2008 |
| WO | 2008028149 | A2 | 3/2008 |
| WO | 2008121294 | A1 | 10/2008 |
| WO | 2009035663 | A2 | 3/2009 |
| WO | WO-2009035663 | A2 | 3/2009 |

OTHER PUBLICATIONS

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasy > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp. 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

U.S. Appl. No. 12/399,482, filed Mar. 6, 2009.

U.S. Appl. No. 12/399,625, filed Mar. 6, 2009.

International Search Report and Written Opinion for International App. No. PCT/US2010/036811 dated Sep. 14, 2010 (19 pages).

\* cited by examiner

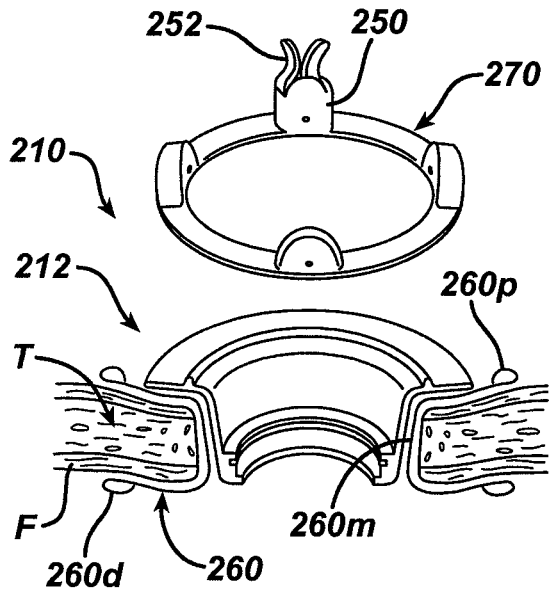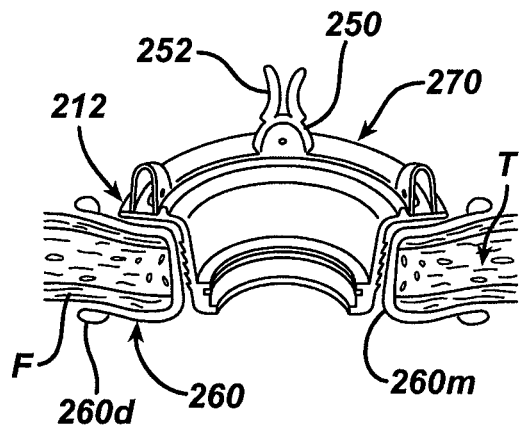
FIG. 12A
FIG. 12B
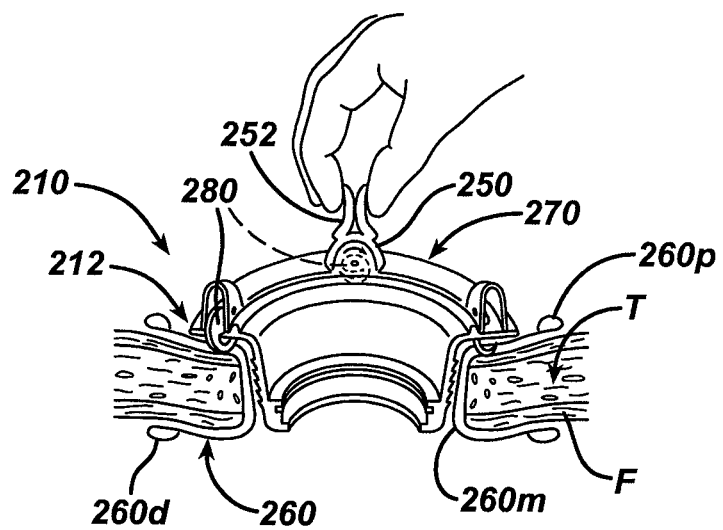
FIG. 12C

FIG. 27
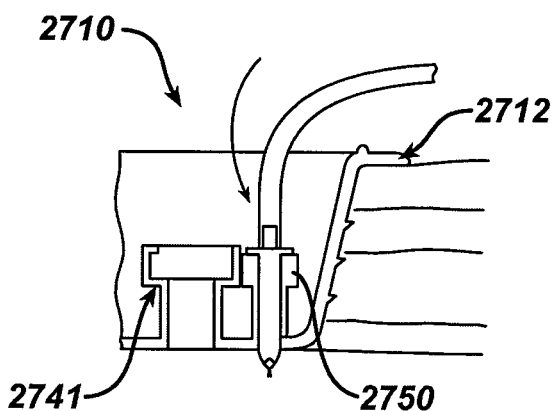
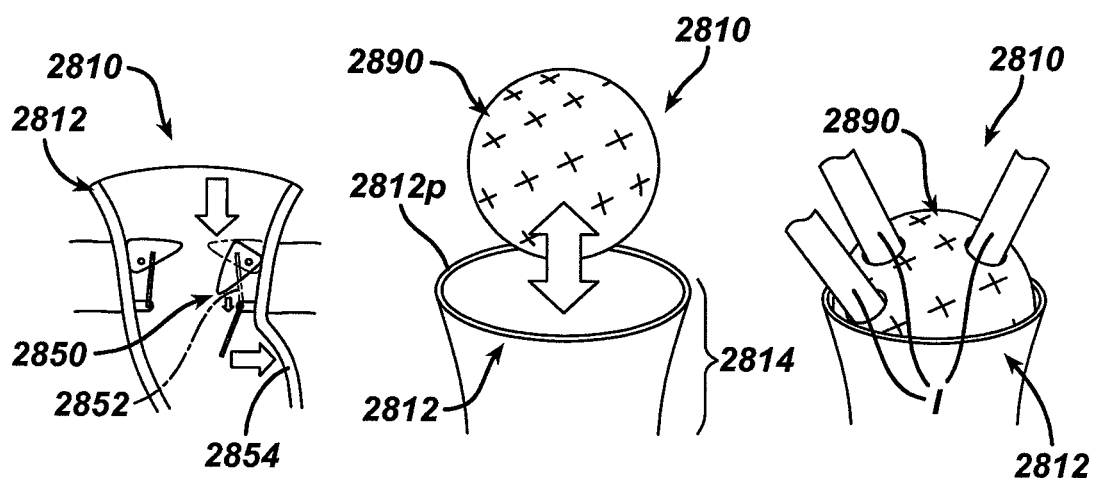
FIG. 28A  FIG. 28B  FIG. 28C

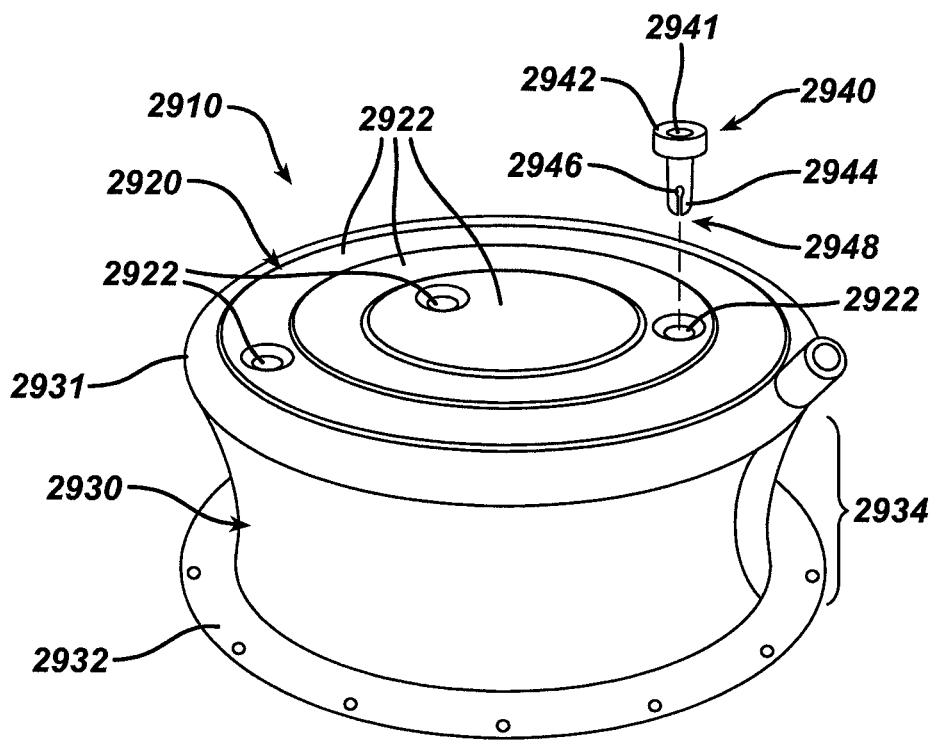
FIG. 29
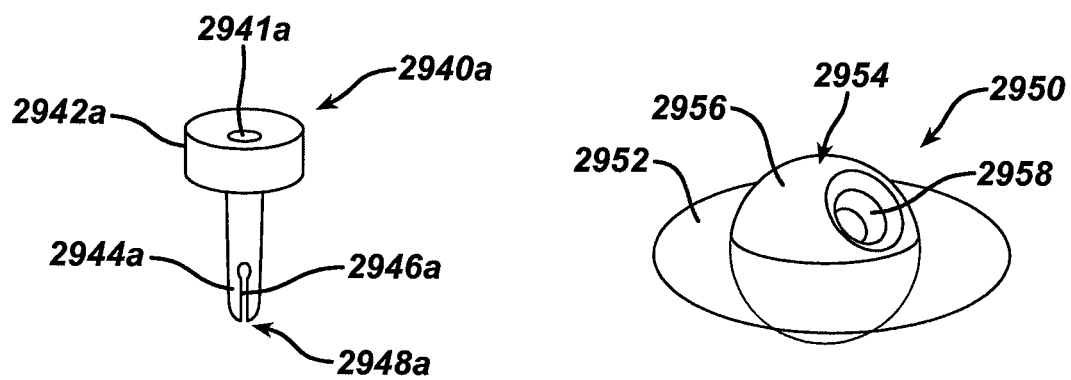
FIG. 30A  FIG. 30B

METHODS AND DEVICES FOR ACCESSING A BODY CAVITY USING A SURGICAL ACCESS DEVICE WITH MODULAR SEAL COMPONENTS

FIELD OF THE INVENTION

The present invention relates to methods and devices for performing surgical procedures, and in particular to methods and devices for accessing a body cavity.

BACKGROUND OF THE INVENTION

Minimally invasive surgical techniques such as endoscopies and laparoscopies are often preferred over traditional open surgeries because the recovery time, pain, and surgery-related complications are typically less with minimally invasive surgical techniques. In many laparoscopic procedures, the abdominal cavity is insufflated with carbon dioxide gas to a pressure of approximately 15 mm Hg. The abdominal wall is pierced and a cannula or trocar that is approximately 5 to 10 mm in diameter is inserted into the abdominal cavity. Typically multiple cannulas or trocars are inserted and placed at the surgical site so multiple instruments, such as laparoscopic telescopes, graspers, dissectors, scissors, retractors, etc., can be used at the same time. While miniaturized versions of laparoscopic procedures have also been developed, the instruments for such procedures are generally more expensive and fragile, and still typically require the use of multiple instruments or channels that have diameters of about 2 to 3 mm.

Because of the rise in popularity of minimally invasive surgeries, there has been significant development with respect to the procedures and the instruments used in such procedures. For example, in some procedures a single incision at the navel can be sufficient to provide access to a surgical site. This is because the umbilicus can be a preferred way to access an abdominal cavity in a laparoscopic procedure. The umbilical incision can be easily enlarged without significantly compromising cosmesis and without significantly increasing the chances of wound complications, thus allowing multiple instruments to be introduced through a single incision. However, a "chopstick" effect can occur which causes interference between the surgeon's hands and the instruments. This interference greatly reduces the surgeon's ability to perform a desired procedure.

Some surgical access devices have been developed to try and reduce the "chopstick effect." For example, a device can include a chamber having a plurality of separate sealing channels that are configured to access a surgical location. Each sealing channel can be configured to receive an instrument and can seal the outside environment from the surgical location. Current devices designed to alleviate the "chopstick effect," however, have their own unique problems. The location and size of the sealing channels can limit use of the device to specific instruments or to a specific procedure. If a different instrument is needed that cannot fit within the sealing channels, the entire device may need to be removed which can increase the length and complexity of the procedure.

Further, because insufflation is generally used as part of laparoscopic procedures, a resulting force is applied to the cannula that causes the cannula to be undesirably pushed in a direction out of a body, like a cork in a pressurized liquid bottle. While the assemblies can generally be sutured in place, the retention and stability capabilities of such assemblies are weak. Additionally, because the cannula is sutured to the tissue, removing the cannula during the course of the surgical procedure is both difficult and inconvenient. Thus, a surgeon is typically unable to easily remove objects from the surgical site or to use different types of cannulas during a single procedure.

Accordingly, there is a need for improved methods and devices for accessing a surgical site during a laparoscopic procedure. There is additionally a need for procedures and devices that allow access devices to be easily removed from a surgical site and replaced during a surgical procedure.

SUMMARY OF THE INVENTION

The present invention generally provides methods and devices for providing surgical access into a body cavity. In one exemplary embodiment, a surgical access device is provided that includes a hollow tubular member that is configured to be positioned in an opening in tissue and that has proximal and distal ends and a sidewall defining a lumen. In addition, a modular seal member that is configured to radially span the lumen of the tubular member can be removably and replaceably matable to a portion of the tubular member.

The surgical access device can be positioned, secured, or affixed within an opening in tissue in any number of ways. In some embodiments, the hollow tubular member can include at least one tissue connector configured to secure a portion of the tubular member to tissue. In other embodiments, the hollow tubular member can be received within a passageway in a flexible retractor that is positioned in an opening in tissue.

The surgical access device and its components can have various configurations. In one embodiment, the modular seal member can be configured to receive at least one access port. For example, the seal member can include a continuous puncturable membrane. The device can also include a plurality of access ports, each of which is configured to mate with the puncturable membrane at a respective desired location. The access ports can have any number of configurations, for example, each access port can have a sealing element that is configured to receive and form a seal around an instrument inserted therethrough. In some embodiments, the access ports can be configured to penetrate the puncturable membrane. The configuration of the access ports can vary in any number of ways. For example, any one or more of the port diameter, port length, port shape, and port stiffness can vary and each of the access ports can have different characteristics.

In other embodiments, the modular seal member can have a plurality of mounts pre-formed therein at predetermined locations, each mount being configured to receive an access port. In some embodiments, a plurality of access ports can be matable within and/or on the mounts. The access ports mounted to the mounts can also vary in any number of ways. For example, any one or more of the port diameter, port length, port shape, and port stiffness or the access ports can vary and each of the access ports can have different characteristics. In some embodiments, the mounts can be moveable relative to one another.

In another exemplary embodiment, a surgical access kit is provided that includes a hollow tubular member having proximal and distal ends and a side wall defining a lumen. The hollow tubular member can be configured to be positioned in an opening in tissue. In some embodiments, the kit can include at least one tissue connector configured to secure a portion of the tubular member to tissue.

In some embodiments, the surgical access kit can also include at least one continuous, puncturable seal member removably and replaceably matable with the tubular member and configured to seal the lumen. A plurality of access ports can also be provided, each of which can be configured to mate with the puncturable membrane at a respective desired location in a sealing engagement. Each access port can have a sealing element and can be configured to receive and form a seal around an instrument inserted therethrough. In some embodiments, at least one of the plurality of access ports is configured to penetrate the puncturable membrane.

In other embodiments, the surgical access kit can also include at least one modular seal member removably and replaceably matable with a portion of the tubular member. The seal member can have at least one mount formed therein that is configured to receive an access port. A plurality of access ports can also be provided, each of which can be selectively matable within or on one of the mounts in a sealing engagement.

The access ports in any of the embodiments of the surgical access kit can be configured in any number of ways. For example, any one or more of the port diameter, port length, port shape, and port stiffness or the access ports can vary and each of the access ports can have different characteristics.

Methods for accessing a body cavity are also provided, and in one embodiment the method can include inserting a hollow tubular member within tissue such that a lumen of the hollow tubular member forms a pathway through the tissue and into a body cavity. The method can further include mating a modular seal member to a portion of the tubular member such that the seal member radially spans the lumen of the tubular member. In some embodiments, a surgical instrument can be inserted through the modular seal member to position a distal end of the surgical instrument in the body cavity. In other embodiments, the method can include mating a plurality of access ports to the modular seal member and inserting a surgical instrument through one of the plurality of access ports.

BRIEF DESCRIPTION OF THE DRAWINGS

The invention will be more fully understood from the following detailed description taken in conjunction with the accompanying drawings, in which:

FIG. 12A is a partial sectional perspective view of another embodiment of a surgical access device including a hollow tubular member positioned in tissue and an attachment device;

FIG. 12B is a sectional perspective view of the surgical access device of FIG. 12A showing the attachment device disposed on the hollow tubular member;

FIG. 12C is a sectional perspective view of the surgical access device of FIG. 12B with housing mechanisms of the attachment device being activated;

FIG. 27 is sectional side view of another embodiment of a surgical access device with an insufflation port positioned in tissue;

FIG. 28A is a sectional side view of another embodiment of a surgical access device positioned in tissue;

FIG. 28B is a partial perspective view of the surgical access device of FIG. 28A;

FIG. 28C is another partial perspective view of the surgical access device of FIG. 28A with surgical instruments inserted through the device;

FIG. 29 is a perspective view of another embodiment of a surgical access device;

FIG. 30A is a perspective view of another embodiment of an access port;

FIG. 30B is a perspective view of another embodiment of an access port positioned in a mount;

DETAILED DESCRIPTION OF THE INVENTION

Figure 1:
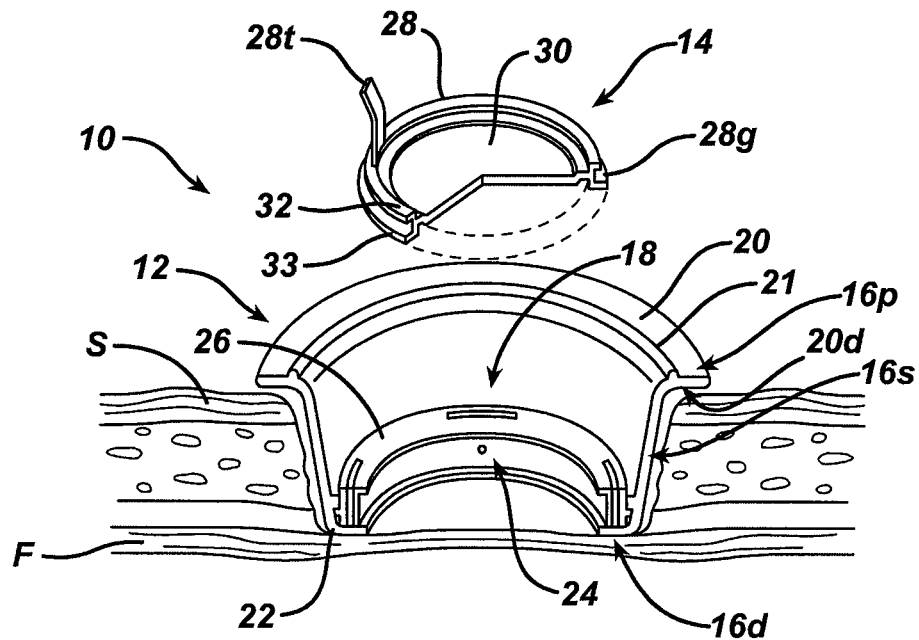
FIG. 1 is a sectional perspective view of a surgical access device including a modular seal member and a hollow tubular member positioned in tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides improved surgical access devices and methods. In use, the surgical access devices disclosed herein can provide access through tissue into a patient's body cavity. The device can include a number of different components, but generally includes a hollow tubular member that can be positionable within an opening in a patient's body and a modular seal member that is configured to radially span a lumen of the tubular member. The access device can also include a plurality of access ports, each of which can be configured to mate with the modular seal member at a respective desired location.

A person skilled in the art will appreciate that the access device can be placed in any opening within a patient's body, whether a natural orifice or an opening made by an incision. For non-limiting example, the access device can be placed through the umbilicus, endoscopically including, vaginally, percutaneously, etc. The elasticity of the skin of the patient can assist in the retention of the access device in the body opening or incision made in the body. In one embodiment, the access device can be substantially flexible so that it can easily be maneuvered into tissue as needed. In such an embodiment, the access device can include a rigid housing or support structure. In other embodiments, the access device can be rigid or semi-rigid. The access device can be formed of any suitable material known in the art, for example silicone, urethane, thermoplastic elastomer, and rubber. In other aspects, the durometer of the materials used to form the access device can vary in different portions of the device. For non-limiting example, a portion of the device that can mate with the modular seal member can be more rigid than a portion of the sidewall of the device.

Typically, during surgical procedures in a body cavity, such as the abdomen, insufflation is provided through the surgical access device to expand the body cavity to facilitate the surgical procedure. Thus, in order to maintain insufflation within the body cavity, most surgical access devices include at least one seal disposed therein to prevent air and/or gas from escaping when surgical instruments are inserted therethrough. Various sealing elements are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel created by the sealing port when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc. A person skilled in the art will also appreciate that any combination of seals can be included in any of the embodiments described herein, whether or not the seal combinations are specifically discussed in the corresponding description of a particular embodiment. Exemplary embodiments of various seal protectors are described in more detail in U.S. Pat. No. 5,342,315 entitled "Trocar Seal/Protector Assemblies," issued Aug. 30, 1994 and U.S. Pat. No. 7,163,525 entitled "Duckbill Seal Protector," issued Jan. 16, 2007, which are hereby incorporated by reference in their entireties.

Any and all embodiments of a surgical access device can also include one or more safety shields positioned through, in, and around any of the components and/or tissue to protect the components against puncture or tear by surgical instruments being inserted through the device. Exemplary embodiments of safety shields are described in more detail in U.S. Patent Publication No. 2006/0247673 entitled "Multi-port Laparoscopic Access Device" filed Nov. 2, 2006, U.S. patent application Ser. No. 12/399,625 entitled "Methods and Devices for Providing Access to a Body Cavity" filed on Mar. 6, 2009, U.S. patent application Ser. No. 12/399,482 entitled "Methods and Devices for Providing Access to a Body Cavity" filed on Mar. 6, 2009, and U.S. patent application Ser. No. 12/242,765 entitled "Surgical Access Device" filed on Sep. 30, 2008, which are hereby incorporated by reference in their entireties.

In any and all of the surgical access device embodiments disclosed herein, an engagement and/or release mechanism can be included to allow certain components of the surgical access device to be removable as needed, such as removable coupling seal member. Any engagement and release mechanism known in the art, e.g., a snap-lock mechanism, corresponding threads, etc., can be used to releasably mate components of the device. Exemplary embodiments of an engagement and release mechanisms are described in more detail in previously mentioned U.S. patent application Ser. No. 12/242,765 entitled "Surgical Access Device" filed on Sep. 30, 2008, U.S. patent application Ser. No. 12/399,625 entitled "Methods and Devices for Providing Access to a Body Cavity" filed on Mar. 6, 2009, and U.S. patent application Ser. No. 12/399,482 entitled "Methods and Devices for Providing Access to a Body Cavity" filed on Mar. 6, 2009 and in U.S. Pat. No. 7,371,227 entitled "Trocar Seal Assembly," issued May 13, 2008 and U.S. Pat. No. 5,628,732 entitled "Trocar With Improved Universal Seal," issued May 13, 2007, which are hereby incorporated by reference in their entireties.

Figure 2:
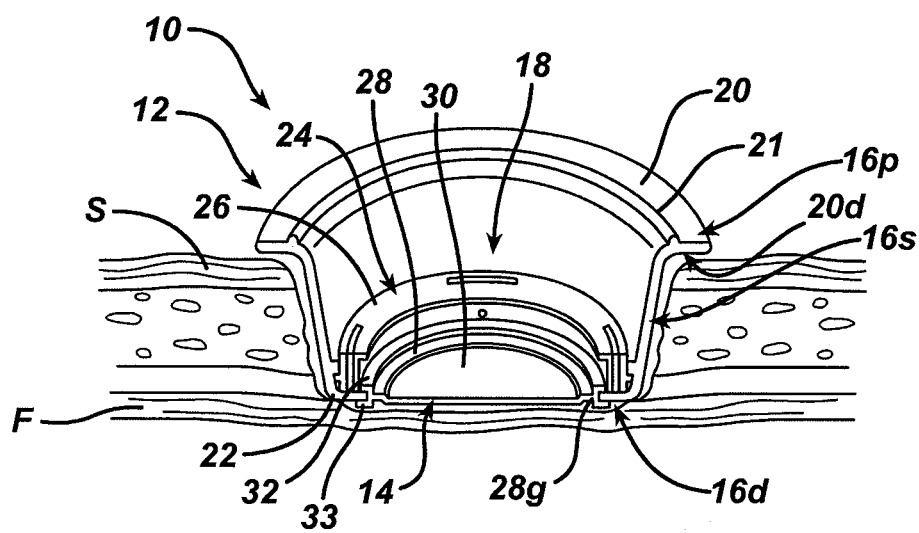
FIG. 2 is a sectional perspective view of the surgical access device of FIG. 1 showing the modular seal member mated with the hollow tubular member.

FIGS. 1 and 2 illustrate one exemplary embodiment of a surgical access device 10 that generally includes a hollow tubular member 12 and a modular seal member 14. The hollow tubular member 12 includes a distal end 16d, a proximal end 16d, and a side wall 16s that extends between the distal and proximal ends. The sidewall 16s defines a lumen or working channel 18 through which instruments can be inserted from outside the body to an interior body cavity. The hollow tubular member can have any diameter, e.g., between about 10 to 60 mm, and any length, e.g., between about 1.5 to 7 cm.

In some embodiments, the proximal end of the hollow tubular member can include a proximal rim or flange that extends radially outward from a proximal end of the hollow tubular member such that the diameter of the proximal rim can be larger than a nominal diameter of the hollow tubular member. In the embodiment shown in FIGS. 1 and 2, the proximal end 16p of the hollow tubular member 12 includes a proximal rim or flange 20 that can be seated against a tissue surface S. The proximal rim 20 can have a variety of configurations, but can generally be effective to prevent the hollow tubular member 12 from passing through an incision in tissue or through a natural orifice into which the hollow tubular member 12 can be inserted. In some embodiments, the rim 20 can be used to anchor the hollow tubular member 12 to tissue using, for non-limiting example, adhesive applied to a distal surface 20d of the rim or flange 20. In other embodiments, the rim 20 can be used in conjunction with an anchoring mechanism, as discussed in more detail below. As illustrated, the proximal rim 20 can include a ridge 21 that can increase the stiffness and strength of the proximal end 16p of the hollow tubular member 12.

In some embodiments, the distal end 16d of the hollow tubular member 12 can also include a rim or flange 22. For example, the distal rim 22 can extend radially inward from the proximal end 16d of the hollow tubular member 12 as shown in FIGS. 1 and 2. The distal rim 22 can have a variety of configurations, as will be discussed in more detail below. In the embodiment shown in FIGS. 1 and 2, the distal rim 22 seats a connection member 24. As shown in the illustrated embodiment, the connection member 24 includes a ring 26 seated on the distal rim 22. However, the connection member 24 can have any number of configurations and can be connected to the distal end 16d of the hollow tubular member 12 in any number of ways. For non-limiting example, the connection member 24 can be connected to the hollow tubular member 12 using a snap-fit, an interference fit, threaded connections, adhesive connections, bayonet connectors, etc. The connection member 24 can be configured to mate with the modular seal member 14.

The modular seal member can also have any number of configurations. As shown in the embodiment illustrated in FIGS. 1 and 2, the modular seal member 14 can include an outer ring 28 and a continuous puncturable membrane 30. The outer ring 28 can have any number of configurations. As shown in the illustrated embodiment, the outer ring 28 can include a groove 28g formed by a first lip 32 and a second lip 33. The first and second lips 32, 33 can be configured in any number of ways. For non-limiting example, the second lip 33 can have a larger diameter than the first lip 32, although any other configuration is possible. The first and second lips 32, 33 can also be flexible so as to allow the lips to deform when the modular seal member 14 is inserted or removed from the hollow tubular member. The groove 28g and lips 32, 33 can engage the hollow tubular member 12, for example, at the distal end 16d of the hollow tubular member 12 by engaging the distal rim 22 or the connection member 24. The engagement can be achieved in any number of ways, some exemplary embodiments of which will be discussed in more detail below. In the embodiment of FIGS. 1 and 2, the groove 28g of the outer ring 28 of the modular seal member 14 engages the distal rim 22 of the hollow tubular member 12 and is retained thereon by the lips 32, 33. The outer ring 28 can also include a tab 28t that can be used configured as a handhold for the modular seal member 14 during insertion and removal from the hollow tubular member 12. The tab 28t can also be used in releasing the lips 32, 33 from engagement with the hollow tubular member 12 and/or connection member 24.

The continuous puncturable membrane 30 disposed in the modular seal member 14 can have any number of configurations. For non-limiting example, the membrane 30 can be formed from a resilient material that can be punctured by an instrument or other implement without tearing or ripping the membrane 30, e.g., latex, silicone rubber, neoprene, polypropylene, polyethylene, isoprene, sanoprene, polyurethane, etc. The continuous puncturable membrane 30 can be joined to the outer ring 28 to form the modular seal member 14 in any number of ways, such as by bonded to the ring 28 with adhesive, ultrasonic welding, heat, etc. In some embodiments, the continuous puncturable membrane 30 can be injection molded onto the ring 28.

In use, the hollow tubular member 12 can be inserted into an opening in tissue. The opening can extend through the tissue to fascia F of the patient's body, as shown in the embodiment in FIGS. 1 and 2, or the opening can extend through the fascia F. As discussed above, the proximal rim 20 can act as a stop to prevent the hollow tubular member 12 from passing through the opening. In some embodiments, the modular seal member 14 can be mated to the hollow tubular member 12 before insertion. In other embodiments the hollow tubular member 12 can be positioned in the tissue and then the modular seal member 14 can be mated to the hollow tubular member 12. Insertion of the hollow tubular member 12 into tissue without the modular seal member 14 connected thereto can allow visualization of the tissue opening's depth and confirmation that the hollow tubular member 12 is properly seated against the fascia F.

Any of the surgical access devices described herein, such as the device of FIGS. 1 and 2, can be positioned within tissue to provide access to a body cavity underlying the tissue. In one embodiment a hollow tubular member 12 can be positioned within a tissue opening such that a lumen of the hollow tubular member 12 forms a pathway through the tissue and into a body cavity. The modular seal member 14 can be mated to a portion of the tubular member 12 either before or after the tubular member 12 is positioned within tissue such that the seal member 14 radially spans the lumen 18 of the tubular member 12. In some embodiments, a surgical instrument can be inserted through the modular seal member 14 to position a distal end of the surgical instrument in the body cavity. In other embodiments, at least one access port can be mated to the modular seal member 14 and a surgical instrument can be inserted through any one or more of the access ports.

The surgical access device 10 can be positioned within an opening formed in the tissue, e.g., in the umbilicus, with the proximal end of the hollow tubular member 12 positioned on the a proximal surface of the tissue. With the surgical access device 10 positioned in the tissue with the modular seal member 14 in place, one or more surgical instruments can be inserted therethrough and into the body cavity, as discussed above, where the instruments can help perform any type of surgical procedure. Any surgical device such as a grasper, a scoping device (e.g., an endoscope, a laparoscope, and a colonoscope), a cutting instrument, etc., can be inserted through the device. A person skilled in the art will appreciate that the term "grasper" as used herein is intended to encompass any surgical instrument that is configured to grab and/or attach to tissue and thereby manipulate the tissue, e.g., forceps, retractors, movable jaws, magnets, adhesives, stay sutures, etc. A person skilled in the art will also appreciate that the term "cutting instrument" as used herein is intended to encompass any surgical instrument that is configured to cut tissue, e.g., a scalpel, a harmonic scalpel, a blunt dissector, a cautery tool configured to cut tissue, scissors, an endoscopic linear cutter, a surgical stapler, etc.

Figure 3:
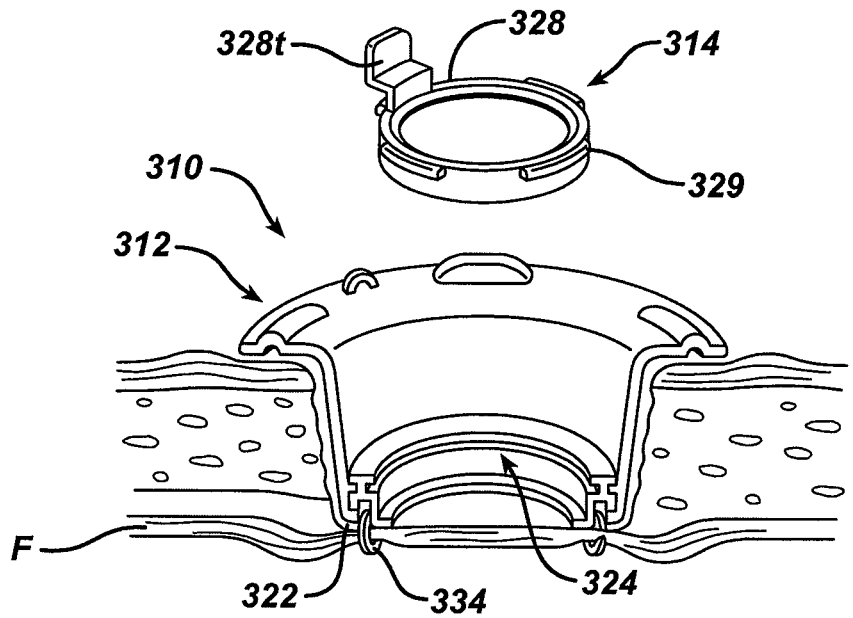
FIG. 3 is a sectional perspective view of another embodiment of a surgical access device including a modular seal member and a hollow tubular member.
Figure 4:
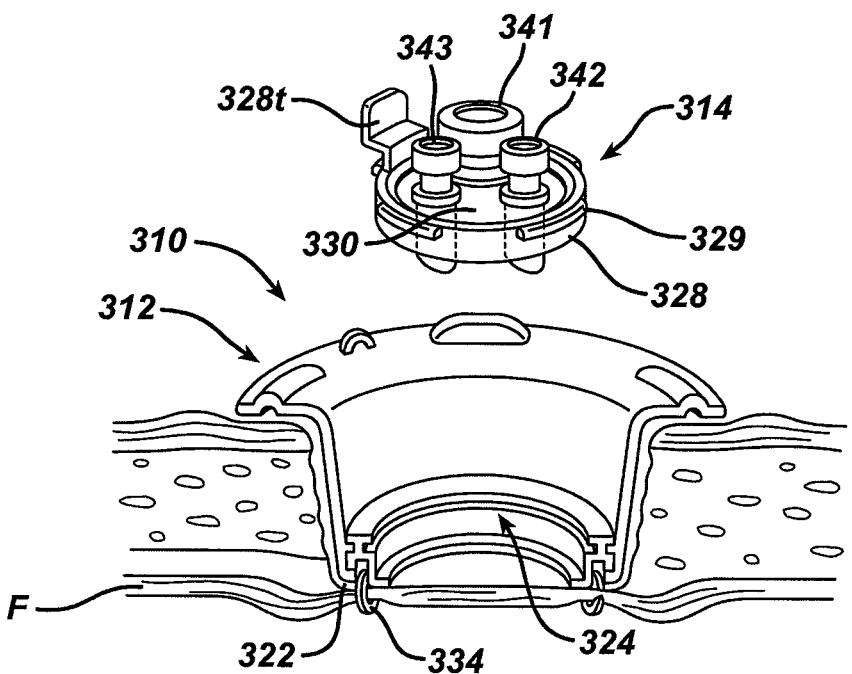
FIG. 4 is a sectional perspective view of the surgical access device of FIG. 3 showing a plurality of access ports mated with the modular seal member.
Figure 5:
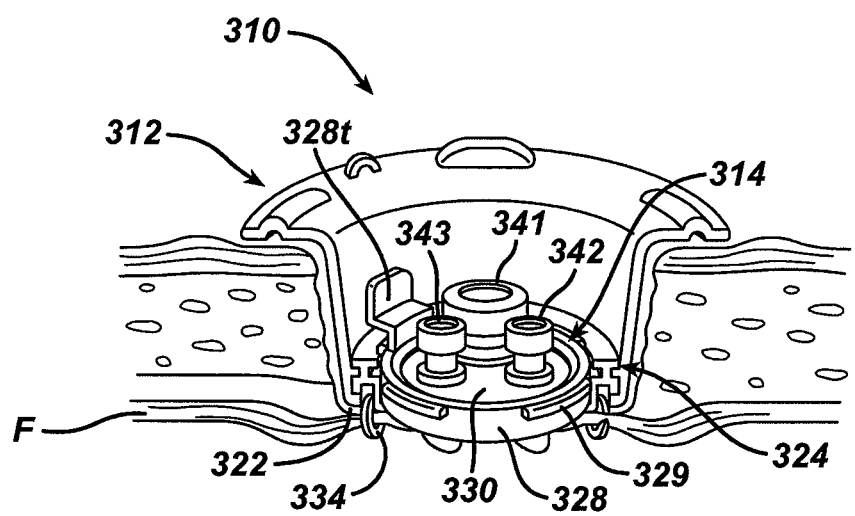
FIG. 5 is a sectional perspective view of the surgical access device of FIG. 4 showing the modular seal member mated with the hollow tubular member.
Figure 8:
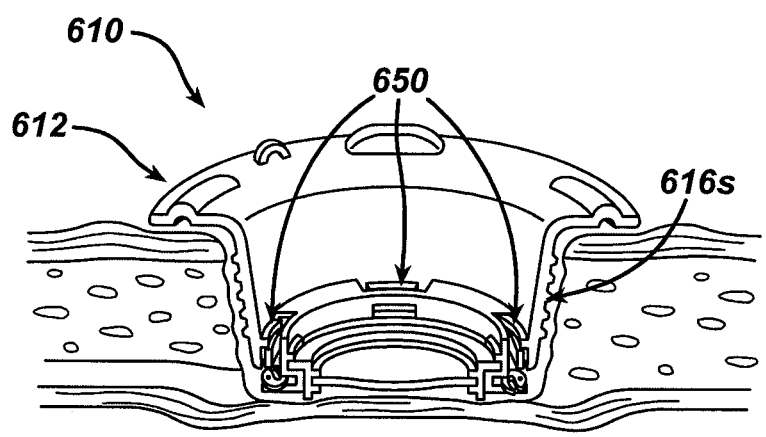
FIG. 8 is a sectional perspective view of the surgical access device of FIG. 7 showing the modular seal member mated with the hollow tubular member.
Figure 9A:
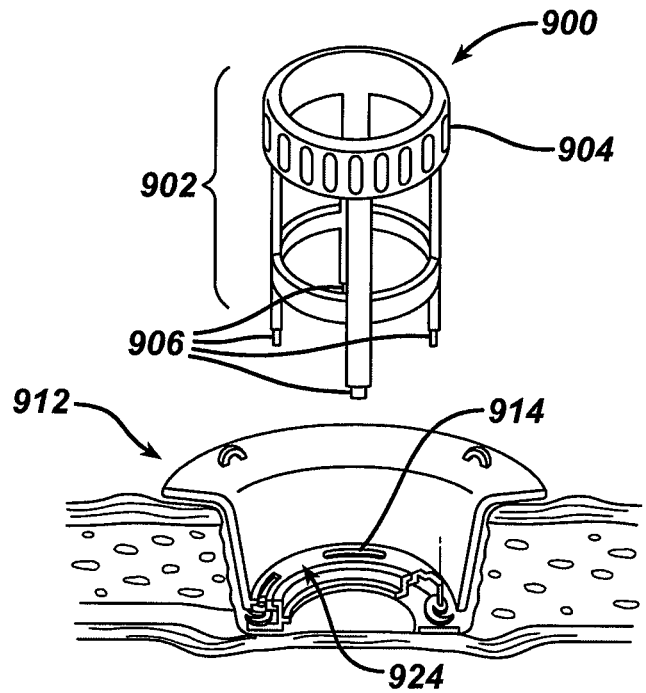
FIG. 9A is a sectional perspective view of another embodiment of a surgical access device including a hollow tubular member positioned in tissue and an attachment tool.
Figure 9B:
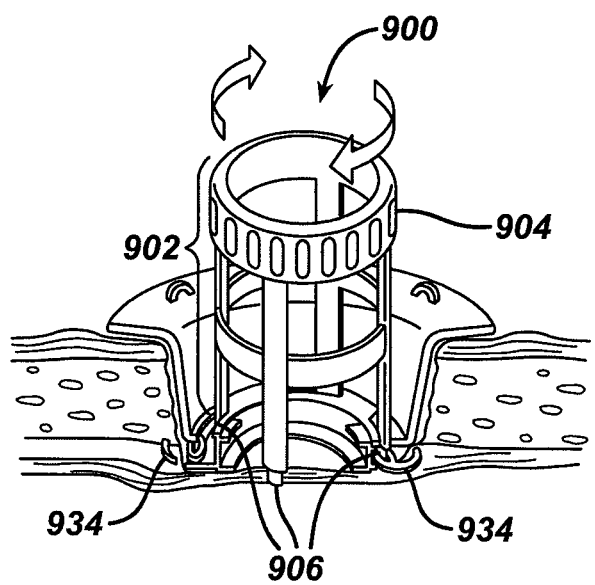
FIG. 9B is a sectional perspective view of the surgical access device of FIG. 9A showing the attachment tool being mated to the hollow tubular member.
Figure 10A:
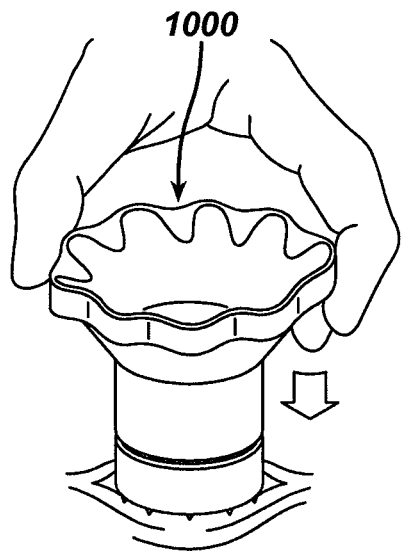
FIG. 10A is a perspective view of another embodiment of an attachment tool being positioned in tissue.
Figure 10B:
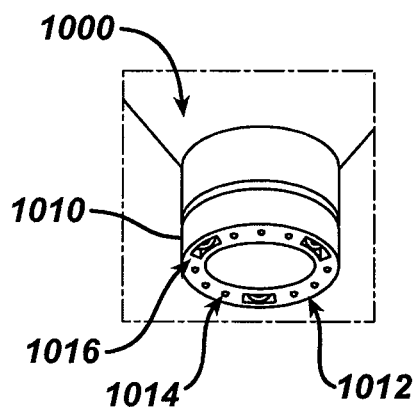
FIG. 10B is a perspective distal view of the attachment tool of FIG. 10A showing attachment features in undeployed positions.
Figure 10C:
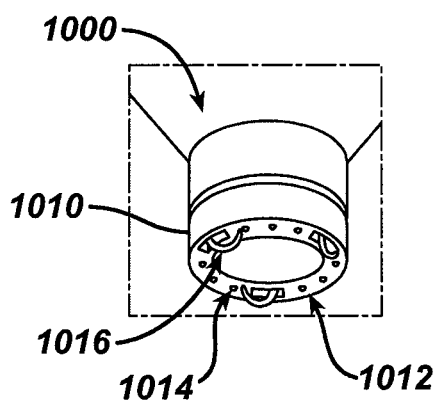
FIG. 10C is another distal perspective view of the attachment tool of FIG. 10A showing the attachment features in deployed positions.
Figure 10D:
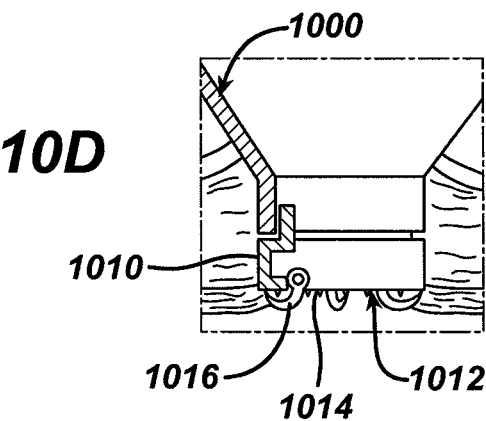
FIG. 10D is a partial sectional perspective view of the attachment tool of FIG. 10A showing the attachment features deployed and engaging tissue.
Figure 11A:
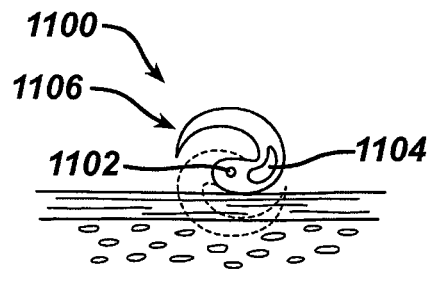
FIG. 11A is a side view of one embodiment of an attachment feature in an undeployed position.
Figure 11B:
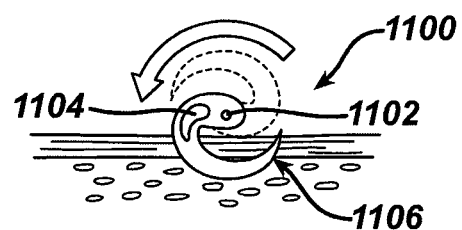
FIG. 11B is a side view of the attachment feature of FIG. 11A showing rotation of the attachment feature into tissue.
Figure 11C:
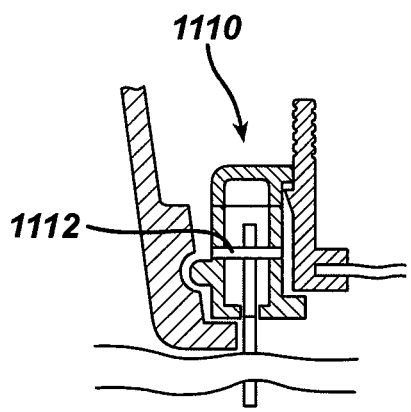
FIG. 11C is a sectional view of the attachment feature of FIG. 11B deployed with a cam member disposed in a hollow tubular member.

In another embodiment illustrated in FIGS. 3, 4, and 5, a connection member 324 of a surgical access device 310 can include attachment features 334 that can lock the hollow tubular member 312 to tissue. The attachment features 334 can be configured in any number of ways. In an exemplary embodiment, the attachment features 334 can be formed as hooks. As illustrated in one embodiment in FIGS. 11A and 11B, hooks 1100 can include a pivot point 1102, a notch 1104, and a pointed engagement region 1106. The hooks 1100 can be rotated by any number of mechanisms. In one embodiment, cam mechanisms can be configured to rotate the hooks 1100 in the direction of the arrow shown in FIG. 11B and into engagement with a tissue surface. FIG. 11C shows an exemplary embodiment of a cam mechanism 1110. The notch 1104 of a hook 1100 can provide a camming surface that can be engaged by a pin 1112 of the cam mechanism 1110 so as to rotate the hook 1100 in response to a linear movement of the pin 1112 from a first position (shown in FIG. 11A) to a second position (shown in FIGS. 11B and 11C). Although the notch 1104 can have any shape and size and be oriented within the hook 1100 in any number of ways, the notch 1104 can be configured such that the hook 1100 is biased to the deployed position when the pin 1112 is in the second position. In the exemplary embodiment of FIGS. 3, 4, 5, the attachment features 334, such as the hook 1100 of FIGS. 11A and 11B, can be configured to distally extend from a distal surface of the surgical access device 310 so as to anchor the device 310 to tissue. However, in other exemplary embodiments, such as one illustrated in FIG. 8, attachment features 634 can be configured to extend approximately perpendicular to a sidewall 616s of a hollow tubular member 612. In the embodiments of FIG. 8, the attachment features 634 can engage tissue proximal to the distal end of the tubular member to anchor the device 610. FIGS. 9A and 9B, discussed below, also show approximately perpendicularly extending attachment features 934.

As shown in the illustrated embodiment of FIGS. 3-5, the attachment features 334 can engage fascia and can pass through openings in a distal rim 322 of the device 310, thereby locking the connection member 324 and the hollow tubular member 312 to the fascia F. The device 310 includes another embodiment of a modular seal member 314 configured to engage the hollow tubular member 312 and that includes a continuous penetrable membrane 330, an outer ring 328, and a tab 328*t*. As shown, the ring 328 can include a lip 329 configured to engage the connection member 324. The lip 329 can be continuous around the circumference of the ring 328 or it can be discontinuous, forming a series of tabs.

FIG. 4 shows the device of FIG. 3 with the addition of a plurality of access ports 341, 342, 343, inserted through the continuous puncturable membrane 330. FIG. 5 shows the modular seal member 314 of FIG. 4 including a plurality of access ports 341, 342, 343 mated with the hollow tubular member 312. As shown, the access ports 341, 342, 343 can provide access to a body cavity through the hollow tubular member 312 when the fully assembled device 310 is positioned in a tissue opening.

Figure 15:
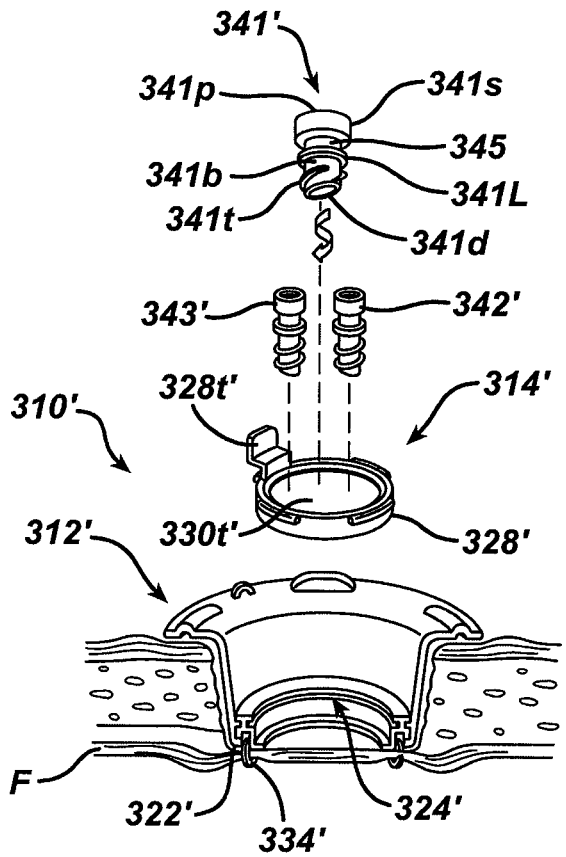
FIG. 15 is a partial sectional perspective view of the surgical access device of FIG. 3 showing the mating of a plurality of access ports with the modular seal member.

The access ports 341, 342, 343 are exemplary embodiments but can have a variety of other shapes, sizes, and configurations. FIG. 15 illustrates other exemplary embodiments of access ports 341', 342', 343' that can be inserted through a puncturable membrane 330' similar to the membrane 330 of FIGS. 3-5. The access ports 341', 342', 343' can be configured in any number of ways, such as being threaded. As shown, the access ports 341', 342', 343', using one access port 341' as an example, can each have a distal end 341*d*, a proximal end 341*p*, and a generally cylindrical body 341*b* extending between the ends 341*d*, 341*p*. The cylindrical body 341*b* can be hollow to allow an instrument to be inserted therethrough and can include various sealing elements such as, for non-limiting example, duckbill seals, cone seals, flapper valves, gel seals, diaphragm seals, lip seals, iris seals, etc. In some embodiments, threads 341*t* can be disposed on a distal portion of the cylindrical body 341*b*. The threads 341*t* can terminate at a circumferential lip 341L proximal to the threads 341*t* such that the access port 341' can have a proximal threadless portion 345. The proximal end 341*p* of the access port 341' can have a larger diameter than the cylindrical body 341*b* and can include a seal housing 341*s*.

The seal housing 341*s* can have a variety of configurations and can include a variety of one or more seal elements that are effective to seal the working channel of the housing when no instrument is disposed therein and/or to form a seal around an instrument disposed therethrough. The seal elements can be particularly useful to prevent gases from escaping through the access port and the housing to maintain the insufflation of the body cavity. Various seals are known in the art, but typically the surgical access device can include at least one instrument seal that forms a seal around an instrument disposed therethrough, but otherwise does not form a seal when no instrument is disposed therethrough; at least one channel seal or zero-closure seal that seals the working channel when no instrument is disposed therethrough; or a combination instrument seal and channel seal that is effective to both form a seal around an instrument disposed therethrough and to form a seal in the working channel when no instrument is disposed therethrough. A person skilled in the art will appreciate that various seals known in the art can be used including, e.g., duckbill seals, cone seals, flapper valves, gel seals, diaphragm seals, lip seals, iris seals, etc.

In some embodiments the distal ends of the access ports 341', 342', 343' can include a sharp tip that can puncture the membrane 330' and/or cut through tissue. In use, the access ports 341', 342', 343' can be inserted through the puncturable membrane 330' by rotating the access ports 341', 342', 343' in the counterclockwise direction of the arrow shown in FIG. 15, although any of the access ports 341', 342', 343' can be configured for clockwise insertion rotation. In some embodiments the modular seal member 314' can be disposed within and mated to the hollow tubular member 312' prior to insertion of the access ports 341', 342', 343'. If this is the case, then rotation of an access port can advance the access port through the puncturable membrane and through tissue to provide access to the body cavity. The access ports 341', 342', 343' can be advanced through the puncturable membrane 330' until the access port's circumferential lip passes through the membrane 330'. The circumferential lips can retain their respective access ports 341', 342', 343' within the membrane 330', thereby providing a seal around the access ports 341', 342', 343'.

Figure 16A:
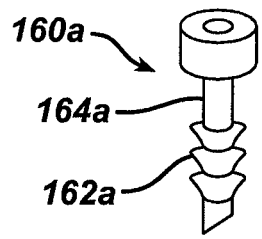
FIG. 16A is a perspective view of an embodiment of an access port for use with a surgical access device.
Figure 16B:
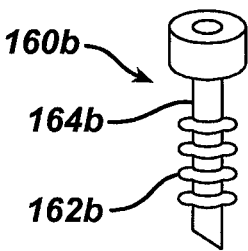
FIG. 16B is a perspective view of another embodiment of an access port for use with a surgical access device.
Figure 16C:
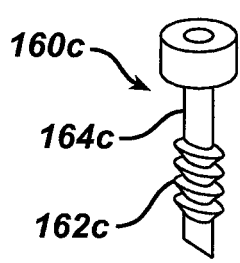
FIG. 16C is a perspective view of another embodiment of an access port for use with a surgical access device.
Figure 16D:
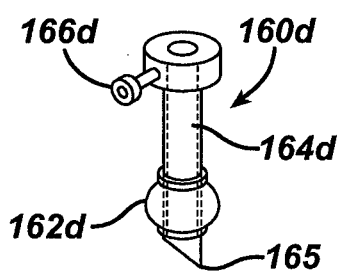
FIG. 16D is a perspective view of another embodiment of an access port for use with a surgical access device.
Figure 16E:
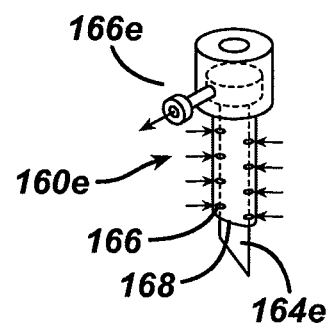
FIG. 16E is a perspective view of another embodiment of an access port for use with a surgical access device.

FIGS. 16A to 16E illustrate other embodiments of access ports having retaining features. Each access port shown in FIGS. 16A to 16E includes a hollow, generally cylindrical body extending between a distal end and a proximal end with the distal ends each including a sharp truncated tip that can enable the access port to be inserted through the puncturable membrane and/or the fascia layer. Also as discussed above, the proximal ends, as shown, can have a larger diameter than the respective cylindrical bodies and can include a seal housing. FIG. 16A to 16C show various surface features disposed on the cylindrical body of the access port. The various surface features can retain the access port within the puncturable membrane and/or the fascia layer. For non-limiting example, a series of conical projections 162a can surround the generally cylindrical body 164a of the access port 160a, as shown in FIG. 16A. Alternatively, a series of annular projections 162b can surround the generally cylindrical body 164b of the access port 160b, as shown in FIG. 16B. FIG. 16C shows another embodiment in which threads 162c can be disposed around the generally cylindrical body 164c of the access port 160c. Other means of retaining an access port within the surgical access device are also possible. For non-limiting example, FIG. 16D shows an access port 160d including an expandable balloon 162d disposed near the distal end 165 of the access port 160d. The expandable balloon 162d can be inflated via an input line 166d using any fluid or gas. The balloon 162d can be affixed to the cylindrical body 164d using any means known in the art. In another embodiment, shown in FIG. 16E, suction can be provided through orifices 166 in a housing 168 surrounding the cylindrical body 164e of the access port 160e. The housing 168 can be in fluid communication with an output line 166e that can be connected to any suction means known in the art.

Figure 17A:
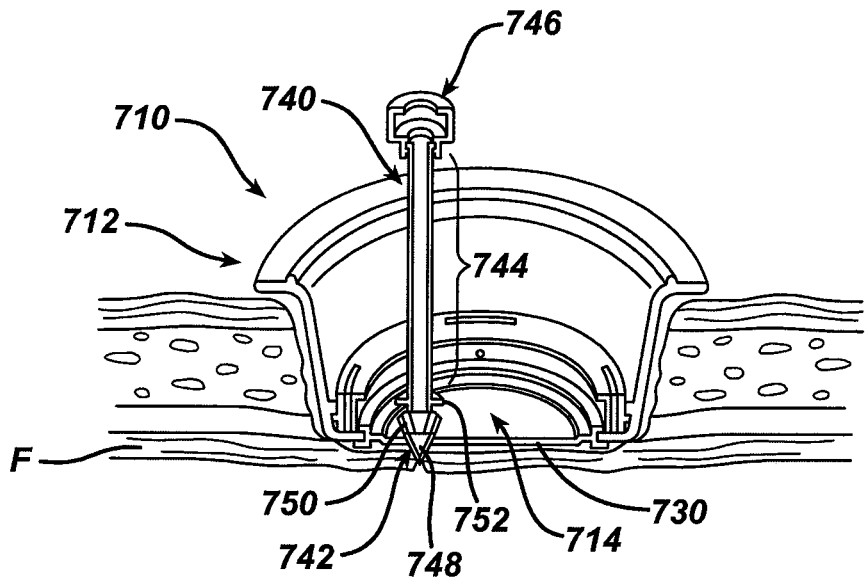
FIG. 17A is a sectional perspective view of another embodiment of a surgical access device showing insertion of an access port and the device positioned in tissue.
Figure 17B:
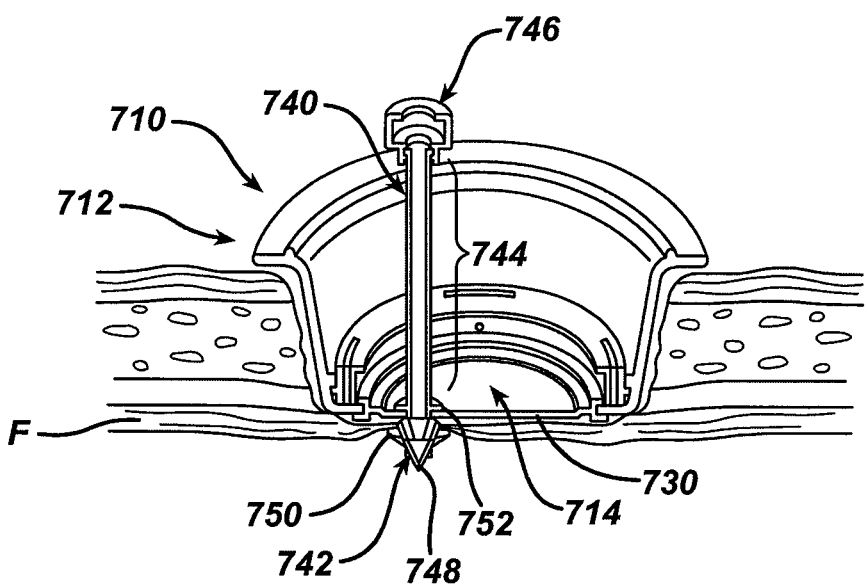
FIG. 17B is another sectional perspective view of another embodiment of a surgical access device showing insertion of an access port and the device positioned in tissue.

In another embodiment, an access port can be inserted through the continuous puncturable membrane and retained therein by expandable retention features. For example, in an exemplary embodiment illustrated in FIGS. 17A and 17B, which shows a surgical access device 710, similar to those described in more detail above, an access port such as a cannula 740 can have a tip region 742 configured to anchor the cannula 740 to the continuous puncturable membrane 730, an elongate shaft region 744, and a proximal seal region 746. However, the cannula 740 can be configured in any number of ways that will be appreciated by one skilled in the art. Although the tip region 742 can also have numerous configurations, in the illustrated embodiment the tip region 742 includes a distal sharpened tip 748, an expandable collar 750, and a clamping collar 752. The cannula 740 can be advanced until the expandable collar 750 passes through the membrane 730 and/or the fascia F. As the tip region 742 passes through an opening formed by the sharpened tip 748, the expandable collar 750 can be compressed to fit through the opening and the cannula 740 can be advanced until the clamping collar 752 contacts the puncturable membrane 730. The expandable collar 750 can then expand to a larger diameter than the hole produced by the sharpened tip 748, as shown in FIG. 17B. The larger diameter of the expandable collar 750 can act to retain the cannula 740 within the opening. The clamping collar 752 can provide a seal against the puncturable membrane 730 to prevent escape of fluid or other material, such as insufflation gases, through the opening in the puncturable membrane 730.

Figure 18:
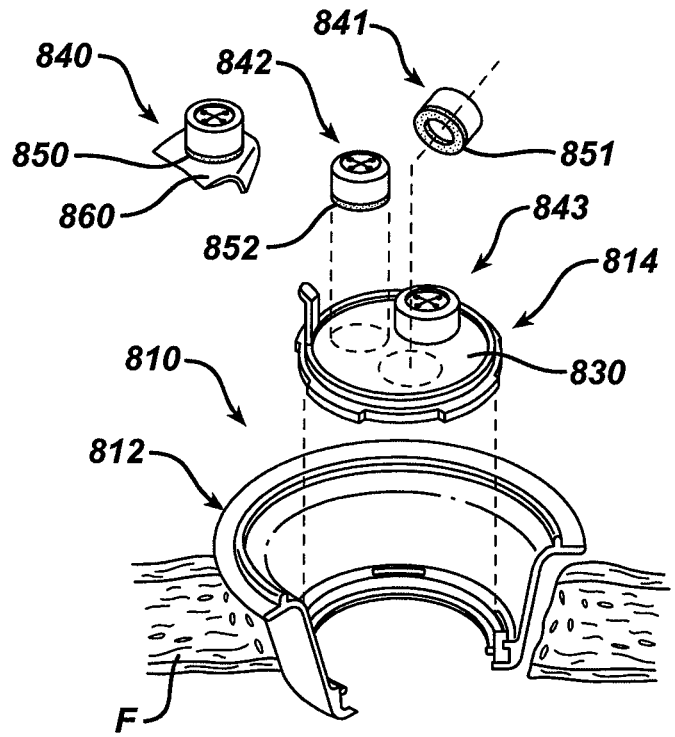
FIG. 18 is a partial sectional perspective view of another embodiment of a surgical access device positioned in tissue and having adhesive access ports.

In some embodiments, access ports can be affixed to the continuous puncturable membrane. In these embodiments, the access ports do not necessarily penetrate the puncturable membrane. In one exemplary embodiment shown in FIG. 18, one or more access ports 840, 841, 842, 843 can be affixed to a continuous puncturable membrane 830 of a surgical access device 810 similar to those described in more detail above. The access port 840, 841, 842, 843 can be affixed to the continuous puncturable membrane 830 using any attachment mechanism, e.g., an adhesive. For non-limiting example, each access port 840, 841, 842, 843 can be provided with an adhesive layer 850, 851, 852 (not shown for access port 843) on a distal surface thereof that can be optionally initially protected by an adhesive backing 860 (only shown for access port 840). When the backing 860 is removed from the access port 840 or adhesive is otherwise exposed, the adhesive layers 850, 851, 852 can be used to mate, join, or affix the access port 840, 841, 842, 843 to the continuous puncturable membrane 830 at respective desired locations. The adhesive can be any adhesive known in the art, e.g., cyanoacrylate, urethane, epoxy, etc. The adhesive 850, 851, 852 can be configured to mate the access port 840, 841, 842, 843 to the puncturable membrane 830 with a bond of sufficient strength to allow an instrument to be inserted through an access port to be manipulated without detaching the access port from the puncturable membrane 830. As shown in FIG. 18, a plurality of access ports 840, 841, 842, 843 can be affixed to the puncturable membrane 830 at various positions to provide customizable access to a body cavity. The access ports 840, 841, 842, 843 can include various sealing elements so as to provide a seal around an inserted instrument. An inserted instrument can pass through one or more sealing elements of the access port and pass through the puncturable membrane 830, and the fascia F if present, to reach a body cavity underlying tissue in which the device 810 is positioned.

Figure 6:
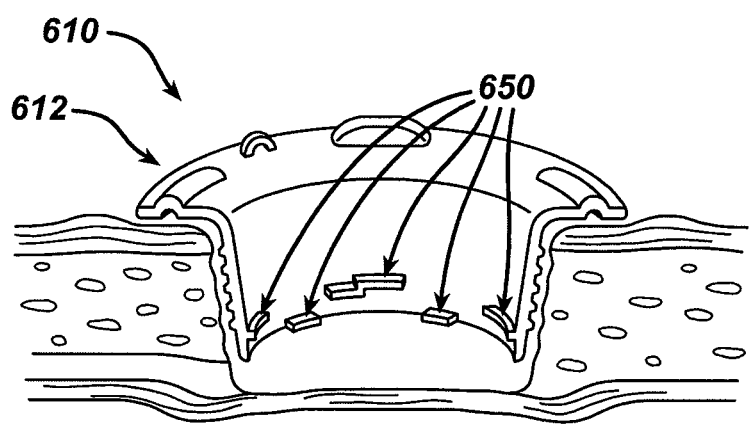
FIG. 6 is a sectional perspective view of another embodiment of a surgical access device including a hollow tubular member positioned in tissue.
Figure 7:
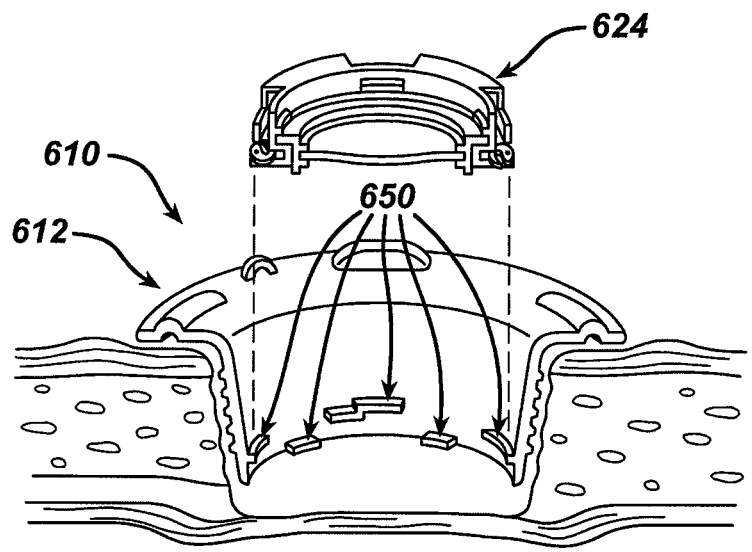
FIG. 7 is a sectional perspective view of the surgical access device of FIG. 6 including a modular seal member.

In another embodiment of a surgical access device shown in FIGS. 6-8, a hollow tubular member of a surgical access device 610 can include a number of projections 650 that can engage complementary projections or grooves on a connection member 624. The projections 650 can be configured in any number of ways, e.g., configured such that rotation of the connection member 624 relative to the hollow tubular member 612 can bring the projections 650 of the hollow tubular member 612 and the connection member 624 into engagement with complementary projections or grooves (not shown) on the connection member 624, thereby mating the connection member 624 to the hollow tubular member 612, as shown in FIG. 8. Rotation of the connection member 624 can be accomplished in any number of ways. For non-limiting example, an attachment tool can be used to rotate the connection member relative to the hollow tubular member. The attachment tool can have a variety of configurations. In one exemplary embodiment shown in FIGS. 9A and 9B, an attachment tool 900 can engage a connection member 924. As in the illustrated embodiment, the attachment tool 900 can have a generally cylindrical body 902 including a proximal handle 904 and one or more distal heads 906. The attachment tool 900 can be hollow to reduce weight and to provide an increased field of view. The attachment tool 900 can rotate the connection member 924 to engage projections 650 (FIG. 7) on the connection member 924 with the hollow tubular member 912. As illustrated in FIG. 9B, the distal heads 906 can extend into one or more slots 914 formed in the connection member 924. The heads 906 can engage various features of the connection member 924 when they are inserted into the slots 914. For non-limiting example, when the tool 900 is rotated in the direction of the arrows shown in FIG. 9B, the heads 906 can engage at least one attachment feature 934 within the connection member 924. For non-limiting example, the tool 900 can deploy attachment features 934, e.g., the hooks 1100 discussed above and shown in FIGS. 11A and 11B.

In some embodiments, an attachment tool can be configured to be removably mated to a connection member so that the attachment tool can be used to insert a surgical access device into an opening in tissue, as shown in an exemplary embodiment illustrated in FIGS. 10A-10D. As shown, an attachment tool 1000 can include an anchoring mechanism 1010 configured to be actuated by rotation of the attachment tool 1000. For non-limiting example, a distal surface of the anchoring mechanism 1010 can include a series of countertraction gripper teeth 1014 having any size, shape, and orientation on the distal surface. The gripper teeth 1014 can be configured to help prevent the anchoring mechanism 1010 from moving or rotating with respect to underlying tissue, such as the fascia layer, when the attachment tool 1000 is rotated. When the attachment tool 1000 is rotated relative to the anchoring mechanism 1010, an attachment feature such as a series of hooks 1016 can be deployed to engage tissue. For non-limiting example, the hooks 1016 can extend from the distal surface 1012 of an anchoring mechanism 1010 from an undeployed position, shown in FIG. 10B, to a deployed position, shown in FIG. 10C. When deployed, the hooks 1016 can help anchor a surgical access device to tissue by gripping and/or penetrating the tissue, thereby preventing unwanted movement during use as shown, for non-limiting example, in FIG. 10D.

FIGS. 12A to 12C illustrate another exemplary embodiment of a surgical access device 210 that includes a flexible retractor 260, a hollow tubular member 212, and a retaining ring 270. In general, the retractor 260 can be configured to be disposed within a tissue opening to form a working channel through tissue T and into a body cavity underlying the tissue T. Although generally referred to as a retractor herein, the retractor can variously be referred to as a wound protector, cannula, ring retractor, or any other member configured to form a pathway through tissue. The retractor 260 can provide access to an interior surgical site within a body cavity and can include proximal and distal ends 260p, 260d and a working channel extending therebetween in a cylindrical mid-portion 260m. The proximal and distal ends 260p, 260d of the retractor 260 can have any suitable configuration that allow the retractor 260 to be secured within the opening. The proximal and distal ends 260p, 260d are depicted as having an annular shape, but they can have any configuration including and without limitation, a circular, oval, elliptical, square, and rectangular configuration. Additionally, the proximal and distal ends 260p, 260d need not be closed or continuous but can, for example, include a plurality of circumferentially-spaced, radially-extending tabs (not shown).

The hollow tubular member 212 can be seated within the working channel of the retractor 260. One skilled in the art will appreciate that the retractor 260 can have any number of configurations, shapes, and sizes depending at least in part on a size of the incision or opening in which the retractor 260 will be disposed, the surgical components with which it will be used, and/or the type of surgical procedure with which it will be used. In an exemplary embodiment, the retractor 260 can be positioned within an opening in tissue such that the distal end 260d of the retractor extends into a patient's body cavity or is adjacent to an inner surface of the tissue with the proximal end 260p of the retractor positioned adjacent to the patient's skin on an exterior surface of the patient's body. The retractor's working channel provides a pathway through the tissue through which surgical instruments can be inserted from outside the body to the interior body cavity.

The retaining ring of the device can be configured in a variety of ways. In the exemplary embodiment illustrated in FIGS. 12A to 12C, the retaining ring 270 can be circular and can have at least one clip housing 250. The clip housing 250 can include a mechanism 252 configured to actuate an attachment mechanism such as a hook 280 similar to the hooks described above. Any number of clip housings 250 can be disposed around the circumference of the retaining ring 270, and they can be spaced around the retaining ring 270 in any number of ways. For non-limiting example, as in the illustrated embodiment, four clip housings 250 can be provided that are spaced equidistant from one another around the circumference of the retaining ring 270. In use, the retaining ring 270 can be applied to the proximal end of the hollow tubular member 212, as shown in FIG. 12B. The clip housing mechanisms 252 can then be actuated as shown in FIG. 12C. Actuation of the clip housings 250 via mechanisms 252 can deploy the hooks 280 such that they pass through the proximal end of the hollow tubular member 212, e.g., through pre-formed openings, and into the tissue T, thereby anchoring the surgical access device 210 to the tissue T.

Figure 13A:
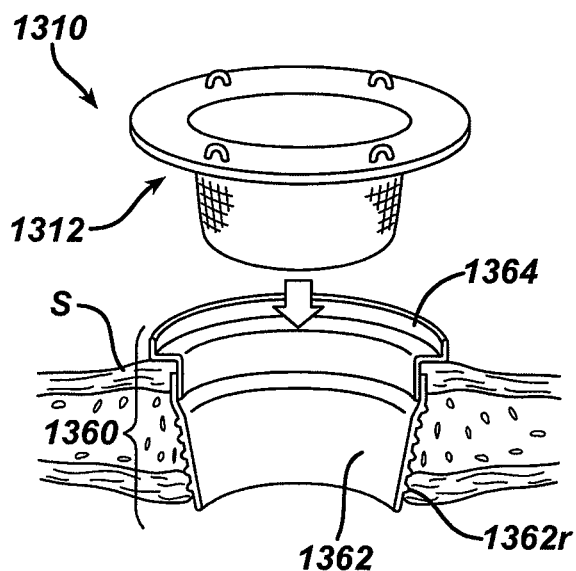
FIG. 13A is a sectional perspective view of another embodiment of a surgical access device including a hollow tubular member and a retractor that is positioned in tissue.

In another embodiment shown in FIG. 13A, a surgical access device 1310 can include a two-part retractor 1360 that includes a proximal ring 1364 and a distal retractor tube 1362. These components can be configured in any number of ways, but in an exemplary embodiment the proximal ring 1364 can be configured to be seated against a tissue surface S and the distal retractor tube 1362 can be configured to sit within an opening in tissue. The proximal ring 1364 and distal retractor tube 1362 can be mated to each other. In some embodiments the proximal ring 1364 can be rigid and the distal retractor tube 1362 can be flexible, although one skilled in the art will appreciate that other variations are possible. As illustrated in FIG. 13A, the outer surface of the retractor tube 1362 can include ribs, threads, or other engagement features 1362r to aid in retaining the retractor within an incision. In use, a hollow tubular member 1312 can be inserted at least partially into a working channel of the assembled retractor 1360 and can engage the retractor 1360 in any number of ways such as by being seated in the proximal ring 1364 and extending into the retractor tube's working channel.

Figure 13B:
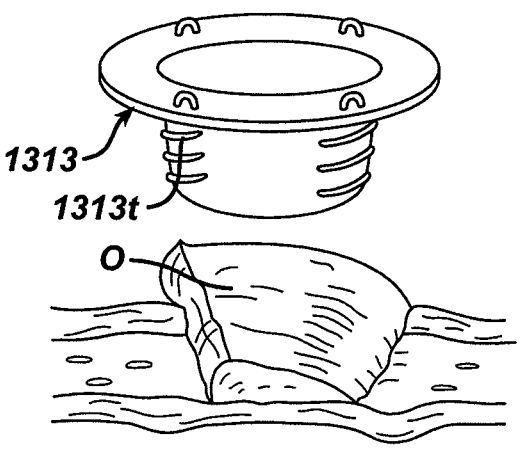
FIG. 13B is a partial sectional perspective view of another embodiment of a surgical access device including a hollow tubular member.

Another exemplary embodiment of a hollow tubular member is illustrated in FIG. 13B. In this embodiment, the outer surface of a hollow tubular member 1313 can include ribs, threads or other engagement features. These engagement features, such as circumferentially spaced threads 1313t shown in FIG. 13B, can be configured to retain the hollow tubular member 1313 within a tissue opening O and/or within a retractor (not shown). In use, the hollow tubular member 1313 can be rotated to advance the hollow tubular member 1313 into the tissue opening O or the retractor to provide a working channel through tissue through which instruments can be inserted.

Figure 14:
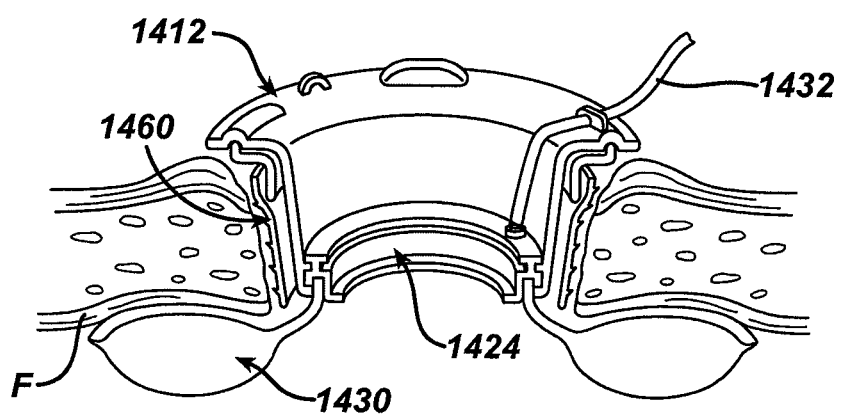
FIG. 14 is a sectional perspective view of another embodiment of a surgical access device having an inflatable anchoring system and being positioned in tissue.

In yet another exemplary embodiment of a surgical access device shown in FIG. 14, a hollow tubular member 1412 can be retained within an opening in tissue using an inflatable bladder 1430. Although the illustrated embodiment depicts the hollow tubular member 1412 and a two-part retractor 1460 similar to that shown in FIG. 13A, one skilled in the art will appreciate that an inflatable bladder 1430 can be used to retain any hollow tubular member within an opening with or without use of a retractor. The inflatable bladder 1430 can be mated to and extend from a connection member 1424 mated to a distal end of the hollow tubular member 1412. The bladder 1430 can have any configuration, such as an annular bladder that, when inflated, expands to a configuration having a diameter larger than a diameter of the hollow tubular member. The bladder can be expanded in any way, such as by inflation from a tube 1432 that can pass through a portion of the connection member 1424. As shown in FIG. 14, when the device including the hollow tubular member having the bladder 1430 is positioned in an opening tissue and the bladder 1430 is expanded, the bladder 1430 can be positioned within a body cavity underlying the tissue against an interior surface of the patient's fascia F. In this way, the inflated or expanded bladder 1430 can retain the hollow tubular member 1412 within the opening in tissue.

Figure 19:
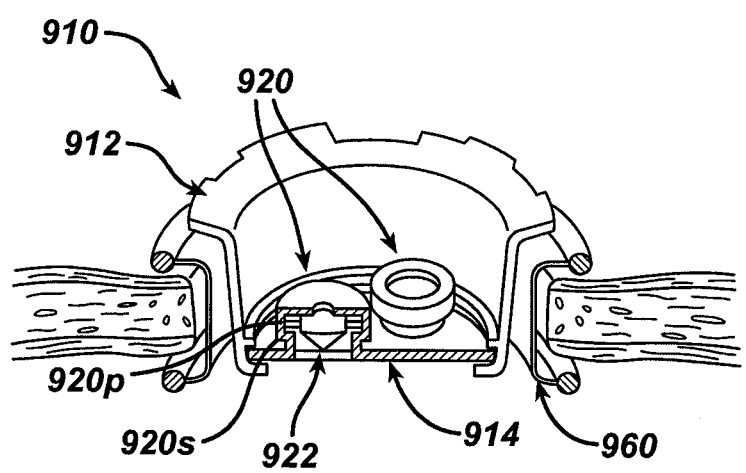
FIG. 19 is a sectional perspective view of another embodiment of a surgical access device with a plurality of mounts positioned in tissue.

In another exemplary embodiment of a surgical access device 910 shown in FIG. 19, a modular seal member 914 of the device 910 can include one or more mounts 920. The mounts 920 can surround openings 922 formed in the modular seal member 914. Although the mounts 920 can be configured in any number ways and can have any size and shape, in the illustrated embodiment the mounts 920 each include a generally cylindrical sidewall 920s extending proximally from the modular seal member 914. Each mount 920 can include an access port 920p mated to the mount 920. As discussed above, the access port 920p can provide a seal around an inserted instrument (not shown). Although in the illustrated embodiment the modular seal member 914 is shown mated to a hollow tubular member 912 that is disposed within a flexible retractor 960 similar to the embodiment of FIGS. 12A to 12C discussed above, one skilled in the art will appreciate that a modular seal member 914 of the type shown in of FIG. 19 can be used with any of the various hollow tubular members and anchoring mechanisms disclosed herein.

Figure 20A:
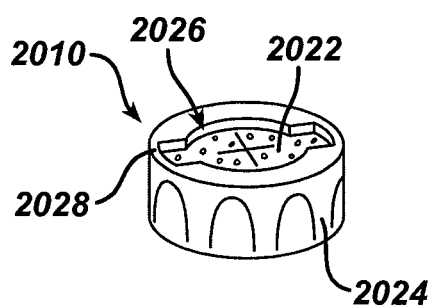
FIG. 20A is a perspective view of one embodiment of an access port for use with a surgical access device.
Figure 20B:
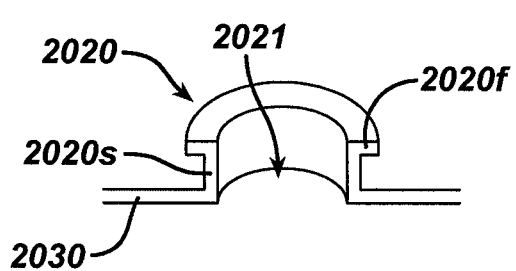
FIG. 20B is a sectional perspective view of one embodiment of a mount for use with a surgical access device.
Figure 20C:
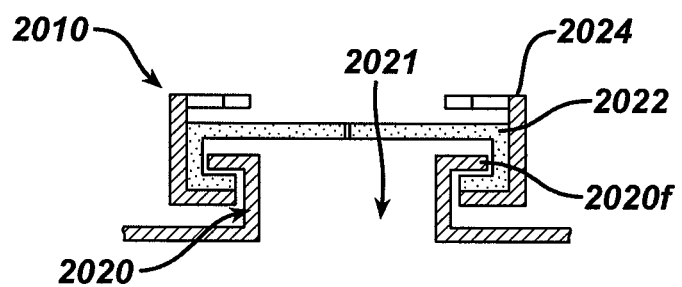
FIG. 20C is a sectional side view of the access port of FIG. 20A mated with the mount of FIG. 20B.

FIGS. 20A to 20C show another exemplary embodiment of an access port 2010 and a mount 2020, similar to of FIG. 19. The access port 2010 can include a sealing element 2022 and a retaining member 2024. The sealing element 2022 can be configured in any number of ways, but in the illustrated exemplary embodiment the sealing element 2022 can span an opening 2026 in the retaining member 2024. The retaining member 2024 can likewise be configured in any number of ways, but as in this exemplary embodiment the retaining member can be generally cylindrical in shape and can have an opening 2026 formed therethrough. The opening 2026 can also be any shape, such as in the illustrated embodiment where the opening 2026 has a generally circular shape with at least one region 2028 of larger diameter. In use, the region 2028 of larger diameter can provide increased range of motion for an inserted instrument without compromising the seal provided by the access port 2010. Although the mount 2020 can be configured in any number ways and can have any shape, as in the illustrated embodiment the mount can include a generally cylindrical sidewall 2020s that extends proximally from a surface 2030, such as a surface of a modular seal member. The sidewall 2020s can define an opening 2021 in the surface 2030 and can terminate in a flange 2020f that can extend circumferentially around the sidewall 2020s. The mount 2020 can be rigid or flexible. As shown in FIG. 20C, the access port 2010 can be coupled to a mount 2020, although the access port 2010 can be mated to any mount, and vice versa. The sealing element 2022 can thereby span the opening 2021 in the mount 2020 to provide a seal around instruments inserted through the mount 2020. Although FIG. 20C shows the mount 2020 and access port 2010 with space therebetween, in use the sealing element 2022 and retaining member 2024 of the access port 2010 can fit tightly against the mount 2020 and its flange 2020f to provide a seal to prevent escape of fluid or other material, such as insufflation gases.

Figure 21:
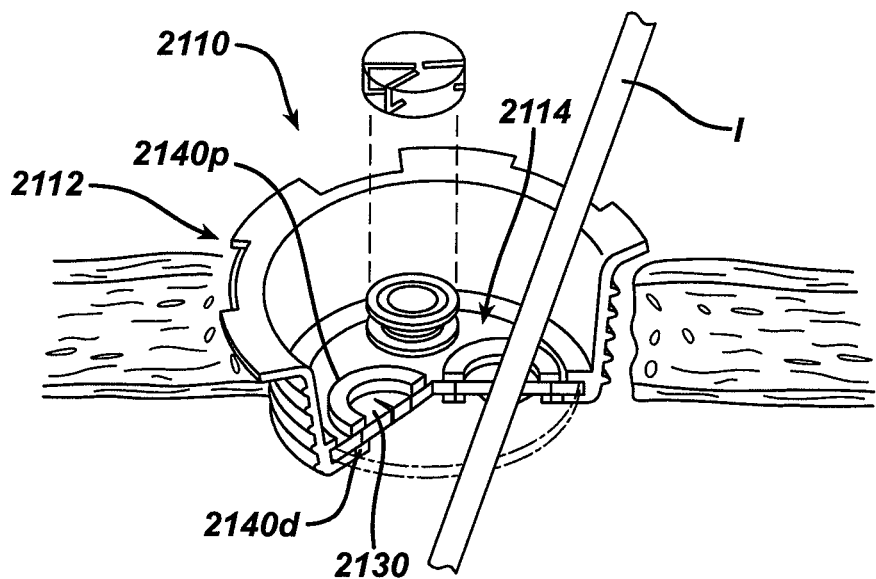
FIG. 21 is a sectional perspective view of another embodiment of a surgical access device positioned in tissue and having puncturable regions.

FIG. 21 shows another exemplary embodiment of a surgical access device 2110 that includes a hollow tubular member 2112 and a modular seal member 2114. In this embodiment, the modular seal member 2114 can include flexible puncturable regions 2130. For non-limiting example, more than one puncturable region 2130 can be formed within a more rigid modular seal member 2114. The puncturable regions 2130 can be formed by removing a portion of the modular seal member 2114 to form an opening which can then be spanned by a puncturable membrane similar to the puncturable membranes discussed above. As shown, the puncturable region 2130 can be retained within an opening in the modular seal member 2114 by proximal and distal rings 2140p, 2140d that can be bonded to the seal member 2124 and/or the puncturable region 2130. The rings 2140p, 2140d can be bonded using any technique known in the art such as, heat welding, adhesives, ultrasonic welding, etc. Alternatively, the puncturable region 2130 can be formed as an integral part of the modular seal member 2114 by any technique, e.g., injection molding, etc. Any number of puncturable regions 2130 can be provided in the modular seal member 2114 along with any of the other sealing elements discussed herein, e.g., sealing elements disposed on mounts, adhesively mounted sealing elements, etc. In use, an instrument I can be inserted through any of the puncturable regions 2130 of the modular sealing element 2114 to provide access to the body cavity. Although only one instrument I is shown inserted through the device 2110, as with any surgical access device described hereon, multiple instruments can be simultaneously and/or sequentially inserted therethrough.

Figure 22:
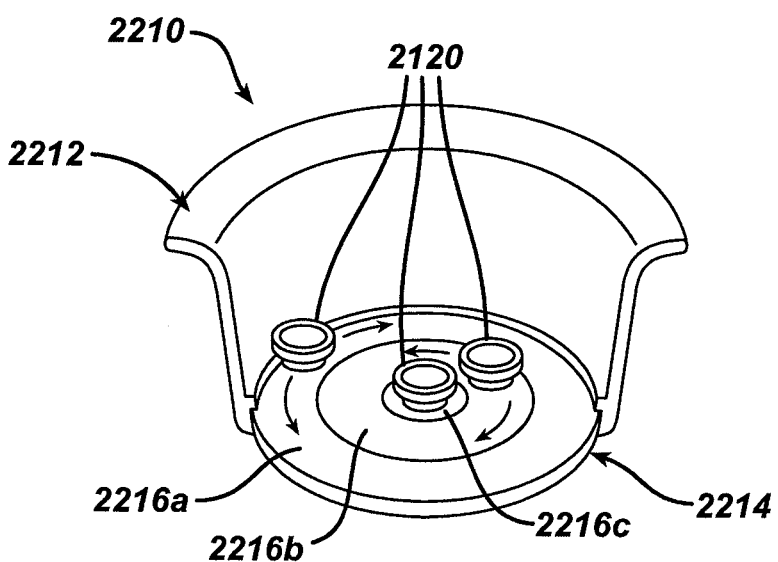
FIG. 22 is a sectional perspective view of another embodiment of a surgical access device with independently moveable mounts.

FIG. 22 illustrates another exemplary embodiment of a surgical access device 2210 that includes a hollow tubular member 2212 and a modular seal member 2214. In this embodiment, the modular seal member can include several access ports 2120, each of which can move independently relative to each other. The independently moveable access 2120 ports can be configured in any number of ways. As in the illustrated embodiment, each access port 2120 can be disposed on an independently moveable concentric ring 2116a, 2116b, 2116c, each of which can rotate independently from the other rings 2116a, 2116b, 2116c. In this manner, each access port 2120 can move independently, thereby providing increased maneuverability of instruments inserted through the access ports 2120. The access ports 2120 can be formed according to any of the embodiments discussed herein such as, for example, access ports with sealing elements disposed on mounts, access ports with adhesively mounted sealing elements, etc.

Figure 23A:
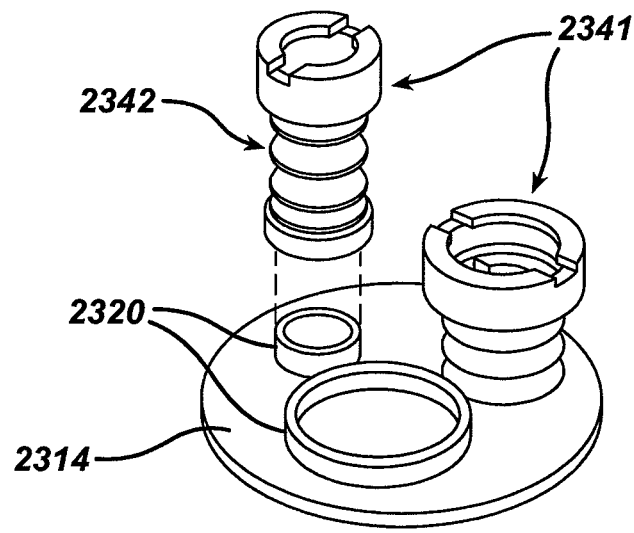
FIG. 23A is a perspective view of another embodiment of a modular seal member having flexible access ports.
Figure 23B:
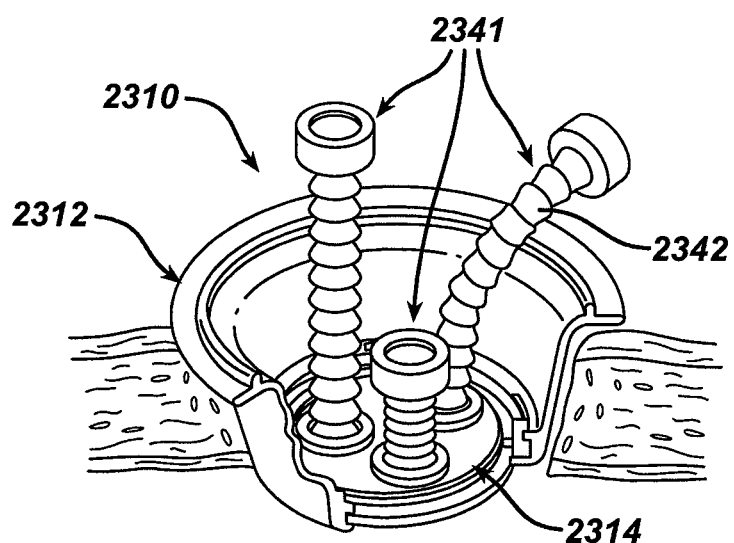
FIG. 23B is a sectional perspective view of another embodiment of a surgical access device positioned in tissue and having flexible access ports.

FIGS. 23A and 23B illustrate yet another exemplary embodiment of a surgical access device 2310 that includes a hollow tubular member 2312, a modular seal member 2314, and one or more access ports 2341. In this embodiment, the access ports 2341 can be connected to the modular seal member 2314 by flexible connectors 2342 that can allow the access ports 2341 to move polyaxially and to longitudinally extend relative to the modular seal member 2314. For non-limiting example, as illustrated in this embodiment, the flexible connector 2342 can be a tubular member that can include one or more bellows that can fold and unfold, thereby allowing the tubular member to flex and extend. FIG. 23A also illustrates an exemplary embodiment of a modular seal member 2314 that can include mounts 2320 or access ports that vary in size or diameter with respect to the other mount(s) or access port(s).

Figure 24:
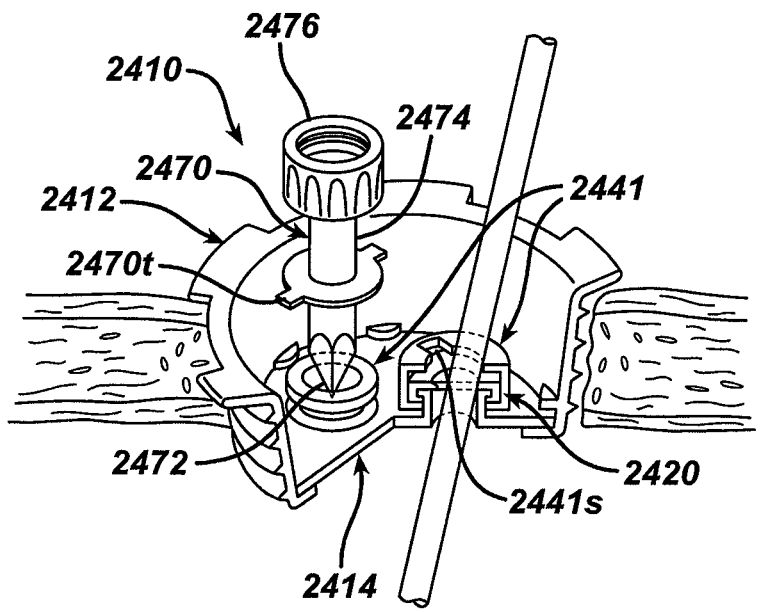
FIG. 24 is a sectional perspective view of another embodiment and a surgical access device with an access port being inserted in the device.

FIG. 24 illustrates another exemplary embodiments of a surgical access device 2410 that includes a hollow tubular member 2412, a modular seal member 2414, and one or more access ports 2441. In this embodiment, a trocar 2470 that includes a pointed tip 2472, an elongate shaft 2474, and a proximal seal housing 2476 can be configured to be inserted through an access port 2441 in the modular seal member 2414. As shown, the seal housing 2476 can be mated to the access port 2441 using one or more tabs 2470t. The tabs 2470t can engage a complementary slot 2441s in the access port 2441 when the seal housing 2476 is rotated, thereby retaining the seal housing 2476 in the access port. In use, the pointed tip 2472 of the trocar 2470 can puncture the modular seal member 2414 or a seal within an access port, and/or the fascia, if present. The trocar 2470 can then pass into a body cavity until the seal housing 2476 makes contact with the access port 2414. The trocar 2470 can then be removed from the modular seal member 2476 to allow an instrument to be inserted through the seal housing 2476 into the body cavity. FIG. 24 also illustrates an embodiment of an access port 2420 disposed on a mount.

Figure 25:
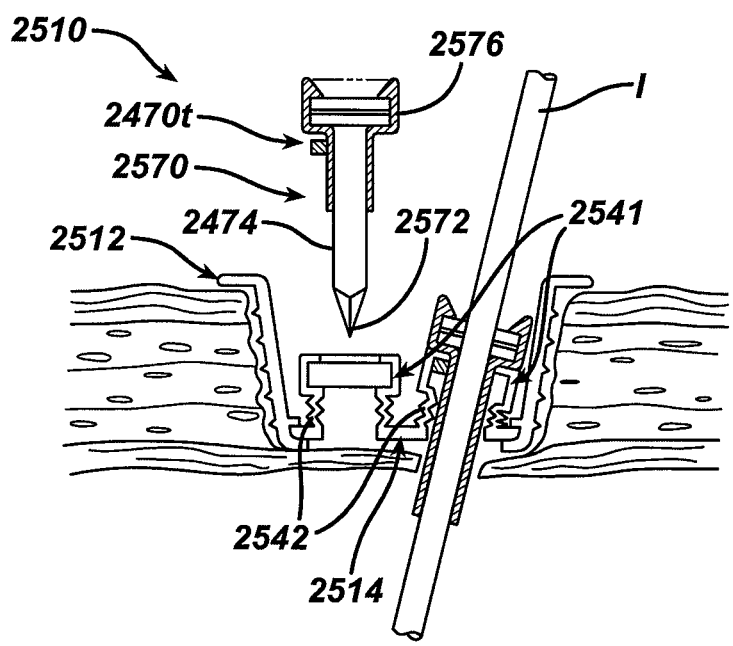
FIG. 25 is a sectional side view of another embodiment of a surgical access device positioned in tissue with an access port being inserted in the device.

FIG. 25 illustrates yet another exemplary embodiment of a surgical access device 2510 that includes a hollow tubular member 2512, a modular seal member 1514, and one or more access ports 2541. In this embodiment, as in FIG. 24, a trocar that includes a pointed tip 2572, an elongate shaft 2474 and a proximal seal housing 2576 can be inserted through an access port 2541 in the modular seal member. In this embodiment, the access ports 2541 can be flexible, similar to the flexible connectors of FIGS. 23A and 23B, discussed above. The distal seal housing 2576 can be mated to a flexible access port 2541 using one or more tabs 2470t. The tab(s) 2470t can engage a complementary slot in the access port 3541 when the seal housing 2576 is rotated, thereby retaining the seal housing 2576 in the access port. In this embodiment, the pointed tip 2572 of the trocar 2570 can be configured to puncture tissue, e.g., fascia, to allow the trocar 2572 to pass into a body cavity underlying the tissue until the seal housing 2576 makes contact with and is engaged with the access port 3541. The trocar 2572 can then be removed from the seal housing 2576 to allow an instrument I to be inserted through the seal housing 2576 into the body cavity. As shown, a flexible mount 2542 can provide increased range of motion of an inserted instrument I by allowing the seal housing 2576 to move relative to the hollow tubular member 2512. One skilled in the art will appreciate that the various seal housings and trocars shown in FIGS. 24 and 25 can pass through and mate with any of the mounts or seal housings disclosed herein.

Figure 26A:
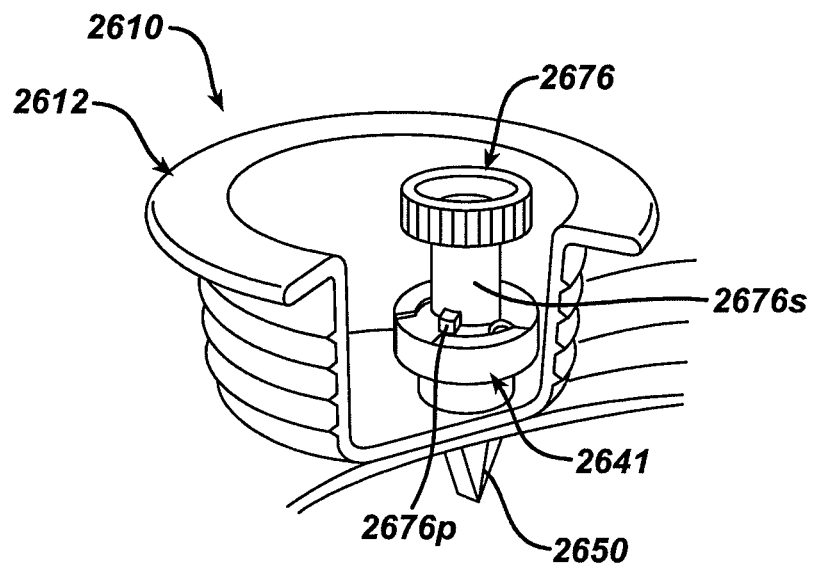
FIG. 26A is a sectional perspective view of another embodiment of a surgical access device with an access device positioned in tissue.
Figure 26B:
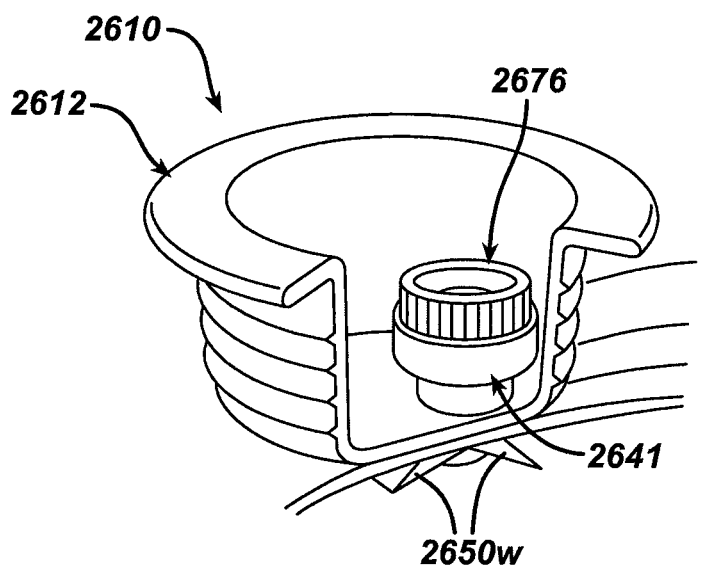
FIG. 26B is sectional perspective view of another embodiment of a surgical access device with an access device positioned in tissue.

In another embodiment, illustrated in FIGS. 26A and 26B, an access port 2676 can be configured to be inserted through a mount 2641 in a hollow tubular member 2612 of a surgical access device 2610. Such insertion of the access port 2676 can cause deployment of an anchoring device 2650 within a body cavity to secure the access port 2676 within the mount 2641. The anchoring device 2650 can be inserted through the mount 2641 in an undeployed configuration (shown in FIG. 26A) and can dynamically move to a deployed configuration (shown in FIG. 26B) when the anchor device 2650 moves into the body cavity. A projection 2676 on a shaft 2676s of the access port 2676 can engage the body of the mount 2641 such that additional force applied to the access port 2676 can deploy one or more wings 2650w that can extend away from the body of the access port 2676 against the hollow tubular member 2612, or fascia, if present. In another embodiment, the anchor device 2650 can be deployed manually after the access port 2676 has been inserted through the mount 2641.

FIG. 27 illustrates an exemplary embodiment of a surgical access device 2710 that includes a hollow tubular member 2712, one or more access ports 2741, and an insufflation port 2750. As shown, the insufflation port 2750 can be molded into the hollow tubular member 2712 or a modular seal member (not shown). Any and all of the surgical access devices described herein can include various ventilation ports to allow evacuation of smoke during procedures that utilize cautery, and/or one or more insufflation ports through which the surgeon can insufflate the abdomen to cause pneumoperitenium, as described by way of non-limiting example in U.S. Patent Application No. 2006/0247673 entitled "Multi-port Laparoscopic Access Device" filed Nov. 2, 2006, which is hereby incorporated by reference in its entirety. The insufflation port can be located anywhere on the device, can have any size, and can accept a leur lock or a needle, as will be appreciated by those skilled in the art.

FIGS. 28A to 28C illustrate another embodiment of a surgical access device 2810 including a hollow tubular member 2812. In this exemplary embodiment, the hollow tubular 1812 member can include an anchoring mechanism 2850. The anchoring mechanism 2850 can include a linkage system 2852 that actuates a retention member 2854. In this embodiment, a spherical sealing ball 2890 can be mated with the proximal end 2852p of the hollow tubular member 2812, as shown in FIGS. 28B and 28C. The spherical sealing ball 2890 can flexible or rigid, and can be puncturable to permit one or more instruments I to be inserted therethrough. The spherical sealing ball 2890 can also be self-sealing. The spherical sealing ball 2890 can be formed from any material or combination of materials known in the art, e.g., gels, rubbers, foams, foamed polypropylene polyurethane, polyethylene, etc. The spherical sealing ball 2890 can be retained within a flared proximal region 2814 of the hollow tubular member 1812 in any number of ways, e.g., frictionally retained, adhesively bonded, mechanically retained by a groove, etc. As shown in FIG. 28C, the one or more instruments I can be inserted through the spherical sealing ball 2890 mated to the hollow tubular member 2812 and into the hollow tubular member 2812 to provide access to a body cavity.

FIG. 29 illustrates another embodiment of a surgical access device 2910 that includes a housing 2920, a retractor 2930, and a modular access port 2940. The retractor 2930 can extend from the housing 2920, and it can be configured to be positioned in an opening formed in tissue. The retractor 29230 can, as shown in this exemplary embodiment, be a substantially flexible member having a proximal flange 2931 and a distal flange 2932 with an inner elongate portion 2934 extending therebetween. The inner elongate portion 2934 can have a diameter less than a diameter of the proximal and distal flanges 2931, 2932 which can have the same diameter or different diameters from one another. A proximal o-ring can be optionally positioned within the proximal flange 2931 to help provide structural support to the retractor within the proximal retractor base. A distal o-ring can optionally be positioned within the distal flange 2932 to provide structural support to the retractor within a patient's body. The proximal and distal o-rings can be substantially flexible or substantially rigid as needed, same or different from one another, for use in a particular application. Any engagement and release mechanism known in the art can be used to releasably mate the housing and the retractor together, for example, the housing can receive the retractor 2930 in a recessed groove around the outer circumference of the housing 2920.

As shown in FIG. 29, the housing 2920 can include one or more concentric rings 2922 that can move independently from each other similar to those discussed above regarding FIG. 22. Each ring 2922 can include one or more openings 2922 configured to receive a modular access port 2940. The modular access ports can be configured in any way and can be any shape and size. As shown in FIGS. 29 and 30A, modular access ports 2940, 2940a can each include a proximal flange 2942, 2942a and a distal clip 2944, 2944a. The proximal flange 2942, 2942a can have a diameter greater than the diameter of the openings in the modular access port 2940, 2940a. The distal clip 2944, 2944a can have a slot 2946, 2946a formed in a distal portion thereof so as to allow the distal tip 2948, 2948a of the clip 2944, 2944a to deform so as to retain the modular access port 2940, 2940a within an opening. For non-limiting example, the deformation of the distal tip 2948, 2948a of the clip 2944, 2944a can provide a frictional engagement with the walls of the opening 2922. For another non-limiting example, the distal tip 2948, 2948a can mechanically engage a clip feature within the opening (not shown). One skilled in the art will appreciate that any mechanical or frictional means known in the art can be employed to retain the modular access port within an opening. The access ports 2940, 2940a can also have an opening 2941, 2941a formed therethrough to allow passage of an instrument. The access ports 2940, 2940a can also include various sealing elements known in the art, e.g., duckbill seals, cone seals, flapper valves, gel seals, diaphragm seals, lip seals, iris seals, etc. as discussed in more detail above. In some embodiments, a gimbal seal 2950, such as that shown in FIG. 30B, can be used. A gimbal seal 2950 can include a frame 2952 that connects a sealing element to a base member. The sealing element 2954 can include a gimbal 2956 and a sealing element 2958 disposed within the gimbal 2956. The gimbal 2956 can rotate and move in all directions within the frame 2952 to allow a full range of movement for a surgical instrument inserted through the sealing element 2958. The sealing element 2958 can form a seal around an instrument inserted therethrough.

Figure 31:
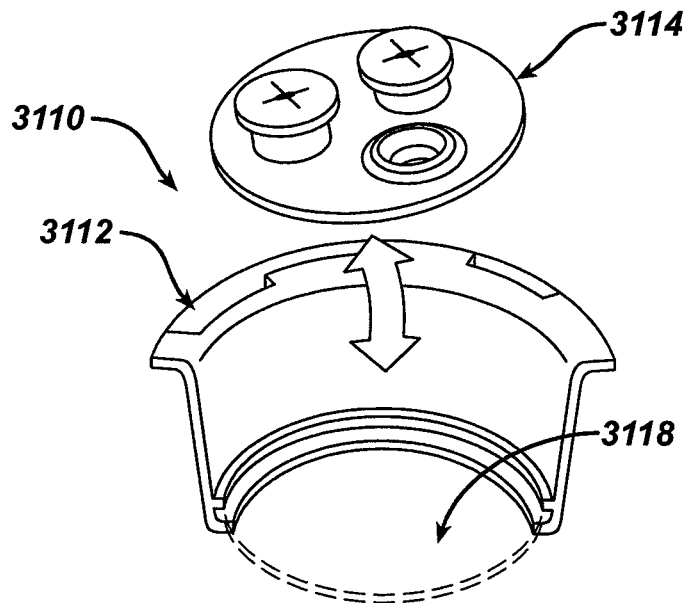
FIG. 31 is a partial sectional perspective view of another embodiment of a surgical access device showing removal of a modular seal member.
Figure 32:
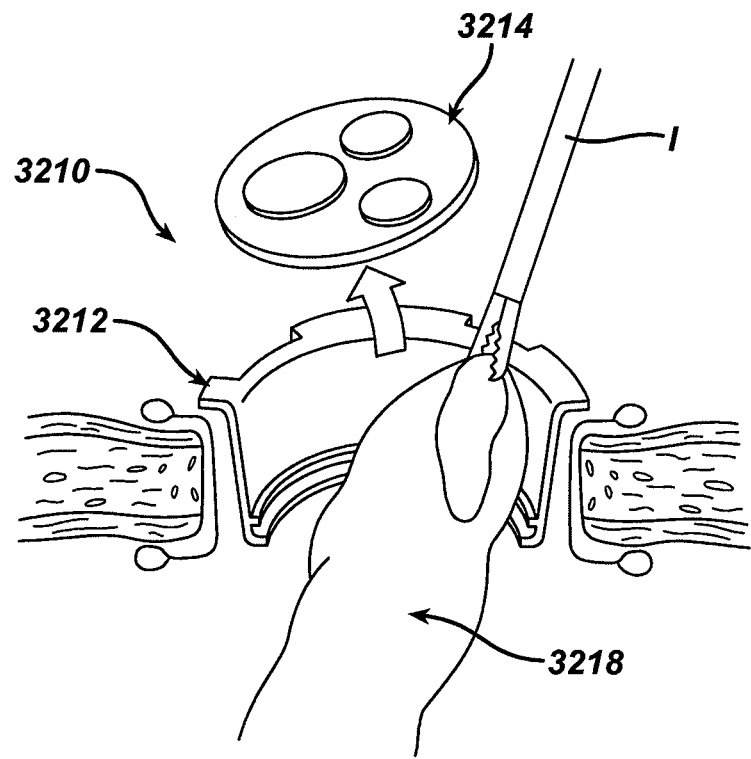
FIG. 32 is a sectional perspective view of another embodiment of a surgical access device positioned in tissue with an instrument inserted therethrough.

At any point before, during, or after a surgical procedure, a modular seal member 3114 of a surgical access device 3110 can be released from a retractor and/or a hollow tubular member 3112 and removed from the device 3110, as shown in one embodiment in FIG. 31. With the modular seal member 3114 of the device 3110 disengaged from the hollow tubular member 3112, the lumen 3118 of the hollow tubular member 3112 can still provide access to a body cavity underlying tissue. As shown in one embodiment in FIG. 32, one or more surgical instruments I can be advanced through a lumen 3218 of the hollow tubular member 3212 with a modular seal member 3214 removed therefrom and can be used to manipulate or remove tissue directly through the lumen 3218 of the hollow tubular member 3212. Any other surgical instrument can be advanced through the lumen 3218, such as a waste removal bag configured to hold waste material, e.g., dissected tissue, excess fluid, etc., for removal from the body cavity. A person skilled in the art will appreciate that one or more surgical instruments can be advanced through the lumen 3218 before and/or after the modular seal member 3214 has been attached to the device 3210.

Figure 33A:
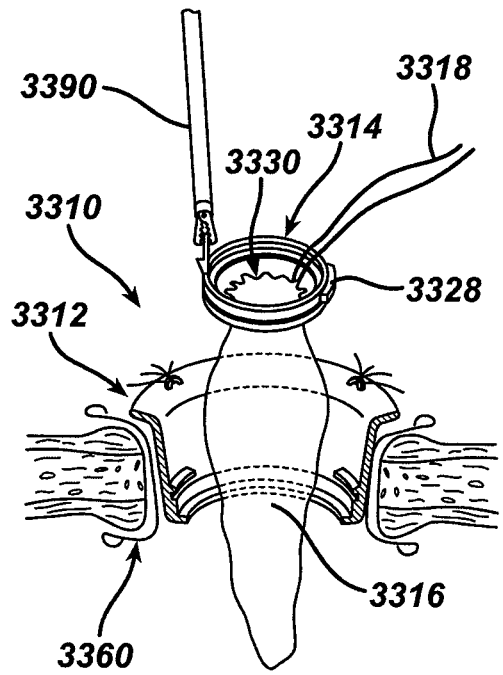
FIG. 33A is a sectional perspective view of another embodiment of a surgical access device with a removable specimen bag being positioned in the device.
Figure 33B:
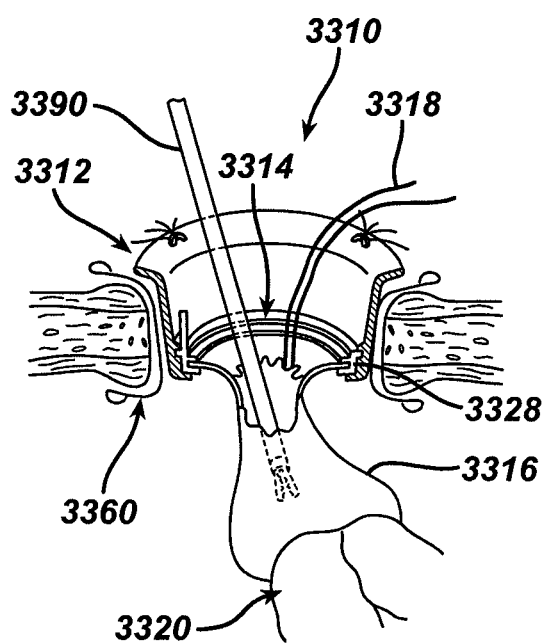
FIG. 33B is a sectional perspective view of the surgical access device of FIG. 33A with tissue being disposed in the removable specimen bag.
Figure 33C:
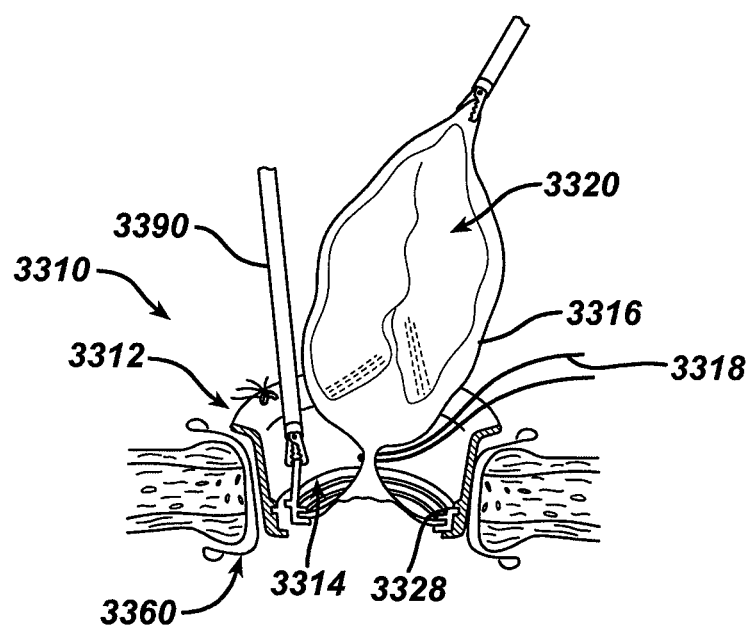
FIG. 33C is a sectional perspective view of the surgical access device of FIG. 33B with the removable specimen bag having tissue disposed therein being removed from the device.

FIGS. 33A to 33C show another exemplary embodiment of a surgical access device 3310 that includes a hollow tubular member 3312, a retractor 3360 and a modular seal member 3314. In this embodiment, the modular seal member 3314 can include a specimen bag 3316 attached directly to an outer ring 3328 configured to mate with the hollow tubular member 3312, as shown in FIG. 33B. The outer ring 3328 can be configured in any number of ways. For non-limiting example, the ring 3328 can include a tab and various grooves that can engage features on the hollow tubular member 3312 as discussed in more detail above. The specimen bag 3316 can be also configured in any number of ways and can be made from any number of materials, such as polyethylene, etc. As in the illustrated embodiment, the specimen bag 3316 can include a draw string 3318 that can be sewn or woven into a proximal portion of the specimen bag 3316.

In use, the specimen bag 3316 and the outer mounting ring 3328 can be inserted into the hollow tubular member 3312. As shown in FIG. 33A, a grasper 3390 can be used to maneuver the ring 3328 into position such that it is mated to the hollow tubular member 3312. A grasper 3390, or other instrument, can then be used to grasp a tissue specimen 3320 through the specimen bag 3316, as shown in FIG. 33B. Using the instrument 3390, the tissue 3320 can be withdrawn through the hollow tubular member 3312, inverting the specimen bag 3316, as shown in FIG. 33C. The specimen bag 3316 can then be closed, for example by tensioning the draw string 3318 to reduce a diameter of the opening 3330 in the bag 3316. One skilled in the art will appreciate that the bag 3316 can be closed by any number of other methods such as heat sealing, twisting, etc. The outer ring 3328 can then be released from the hollow tubular member 3312. In some embodiments, the specimen bag 3316 can be cut from the ring 3328 between the closed opening of the bag 3316 and the ring 3328 to separate the specimen bag 3316 from the ring 3328.

The embodiments described herein can be used in any known and future surgical procedures and methods, as will be appreciated by those skilled in the art.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. This can be done by any number of ways known to those skilled in the art including beta or gamma radiation, ethylene oxide, steam, and a liquid bath (e.g., cold soak). In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
a hollow tubular member having a proximal end, a flexible distal end, and a side wall defining a lumen, the hollow tubular member being configured to be positioned in an opening in tissue of a patient by advancing the flexible distal end through the tissue such that the proximal end is positioned external to the patient and the flexible distal end is positioned within a body cavity of the patient underlying the tissue, the distal end defining a perimeter; and
a modular seal member removably and replaceably mated to the distal end of the tubular member such that when the proximal end of the hollow tubular member is positioned external to the patient and the flexible distal end of the hollow tubular member is positioned within the body cavity, a surgical instrument can be inserted through the lumen from outside the patient, pass through the modular seal member, and extend into the body cavity, the seal member being configured to radially span the lumen of the tubular member, wherein the seal member has a plurality of puncturable regions within an interior region thereof, a remainder of the interior region of the seal member having a rigidity that is greater than a rigidity of each of the plurality of puncturable regions, and each of the plurality of puncturable regions being configured to receive at least one access port punctured therethrough.

2. The device of claim 1, further comprising a flexible retractor configured to be positioned in an opening in tissue and configured to receive the hollow tubular member within a passageway therethrough.

3. The device of claim 1, wherein the tubular member further includes at least one tissue connector configured to secure a portion of the tubular member to tissue.

4. The device of claim 1, further comprising a plurality of access ports, each of which is configured to mate with one of the plurality of puncturable regions, each access port having a sealing element and being configured to receive and form a seal around an instrument inserted therethrough.

5. The device of claim 4, wherein at least one of the plurality of access ports is configured to puncture through the puncturable membrane with a sharp distal tip.

6. The device of claim 4, wherein the access ports have different characteristics selected from at least one of port diameter, port length, port shape, and port stiffness.

7. The device of claim 1, wherein the modular seal member has a plurality of mounts pre-formed therein at predetermined locations, each mount being configured to receive an access port.

8. The device of claim 1, further comprising a plurality of interchangeable modular seal members, each having a plurality of mounts pre-formed therein at predetermined locations, each mount being configured to receive an access port.

9. The device of claim 8, wherein the interchangeable modular seal members have different characteristics selected from at least one of location of mounts, diameter of mounts, length of mounts, shape of mounts, and stiffness of mounts.

10. The device of claim 8, further including a plurality of access ports matable within the mounts.

11. The device of claim 10, wherein the access ports have different characteristics selected from port diameter, port length, port shape, and port stiffness.

12. The device of claim 8, wherein the mounts are movable relative to one another.

13. The device of claim 1, wherein the modular seal member is configured to fluidly seal the lumen when removably and replaceably mated to the distal end of the tubular member before and after the access port is advanced therethrough.

14. A surgical access kit, comprising:
a hollow tubular member having proximal and distal ends and a side wall defining a lumen, the hollow tubular member being configured to be positioned in an opening in tissue;
at least one continuous, puncturable seal member removably and replaceably matable with the tubular member and configured to seal the lumen; and
a plurality of access ports, each of which is configured to mate with the at least one continuous, puncturable seal member by advancing a sharp distal end of the access port through any location on a surface of the at least one continuous, puncturable seal member so as to be in a sealing engagement with the at least one continuous, puncturable seal member, each access port having a sealing element configured to receive and form a seal around an instrument inserted therethrough, and each access port having a proximal head with an elongate body extending distally therefrom, the elongate body having a plurality of retaining features extending radially outward therefrom, the plurality of retaining features being configured to retain the access port within the at least one continuous, puncturable seal member.

15. The surgical access kit of claim 14, wherein at least one of the sharp ends of the plurality of access ports is configured to cut the tissue.

16. The surgical access kit of claim 14, further comprising at least one tissue connector configured to secure a portion of the tubular member to tissue.

17. A surgical access kit, comprising:
a hollow tubular member having a proximal end, a flexible distal end, and a side wall defining a lumen, the hollow tubular member being configured to be positioned in an opening in tissue such that the lumen extends from outside the patient to within a body cavity of the patient with the distal end of the tubular member being positioned in the body cavity;

at least one modular membrane removably and replaceably mated to the distal end of the tubular member and including a plurality of separate predefined puncturable regions, the at least one modular membrane having formed therein a plurality of mounts, each of the mounts being formed such that the mount circumferentially surrounds a respective one of the plurality of puncturable regions, each of the plurality of mounts including a sealing element formed by a respective one of the plurality of separate predefined puncturable regions to provide a fluid seal of the lumen; and a plurality of access ports, each selectively matable within one of the mounts in a sealing engagement such that when the at least one modular membrane is mated to the distal end of the tubular member, each of the access ports extends proximally through the lumen away from the body cavity when the tubular member is positioned in the opening in the tissue, and the fluid seal provided by the sealing elements formed from the at least one modular membrane being maintained whether or not any one or more of the access ports are mated within any of the mounts in the sealing engagement.

18. The surgical access kit of claim 17, wherein the access ports have different characteristics selected from port diameter, port length, port shape, and port stiffness.

19. The surgical access kit of claim 17, further comprising at least one tissue connector configured to secure a portion of the tubular member to tissue.

* * * * *